US009573870B2

(12) United States Patent
Eisenschmid

(10) Patent No.: US 9,573,870 B2
(45) Date of Patent: Feb. 21, 2017

(54) HETEREOCYCLIC AGENT AS CATALYTIC STABILIZING AGENT IN A HYDROFORMYLATION PROCESS

(71) Applicant: Dow Technology Investments LLC, Midland, MI (US)

(72) Inventor: Thomas C. Eisenschmid, S. Charleston, WV (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 14/765,113

(22) PCT Filed: Mar. 7, 2014

(86) PCT No.: PCT/US2014/021510
§ 371 (c)(1),
(2) Date: Jul. 31, 2015

(87) PCT Pub. No.: WO2014/149915
PCT Pub. Date: Sep. 25, 2014

(65) Prior Publication Data
US 2015/0376101 A1 Dec. 31, 2015

Related U.S. Application Data

(60) Provisional application No. 61/790,642, filed on Mar. 15, 2013.

(51) Int. Cl.
*C07C 45/50* (2006.01)
*B01J 31/24* (2006.01)
*B01J 31/02* (2006.01)
*C07D 333/32* (2006.01)

(52) U.S. Cl.
CPC .......... *C07C 45/505* (2013.01); *B01J 31/0244* (2013.01); *B01J 31/24* (2013.01); *B01J 31/2409* (2013.01); *C07C 45/50* (2013.01); *C07D 333/32* (2013.01); *B01J 2231/321* (2013.01); *B01J 2531/822* (2013.01); *Y02P 20/582* (2015.11)

(58) Field of Classification Search
None
See application file for complete search history.

(56) References Cited

U.S. PATENT DOCUMENTS

| | | |
|---|---|---|
| 3,527,809 A | 9/1970 | Pruett et al. |
| 4,148,380 A | 4/1979 | Haraikawa |
| 4,148,830 A | 4/1979 | Pruett et al. |
| 4,247,486 A | 1/1981 | Brewester et al. |
| 4,248,802 A | 2/1981 | Kuntz |
| 4,260,828 A | 4/1981 | Morrell et al. |
| 4,277,627 A | 7/1981 | Bryant et al. |
| 4,283,304 A | 8/1981 | Bryant et al. |
| 4,329,507 A | 5/1982 | Takeda et al. |
| 4,399,312 A | 8/1983 | Russell et al. |
| 4,518,809 A | 5/1985 | Forster et al. |
| 4,528,403 A | 7/1985 | Tano et al. |
| 4,605,780 A | 8/1986 | Billig et al. |
| 4,654,445 A | 3/1987 | Ono et al. |
| 4,668,651 A | 5/1987 | Billig et al. |
| 4,668,824 A | 5/1987 | Jenck et al. |
| 4,710,587 A | 12/1987 | Bryant et al. |
| 4,716,250 A | 12/1987 | Abatjoglou et al. |
| 4,731,486 A | 3/1988 | Abatjoglou et al. |
| 4,774,361 A | 9/1988 | Maher et al. |
| 4,861,918 A | 8/1989 | Miller et al. |
| 4,929,767 A | 5/1990 | Miller et al. |
| 5,110,990 A | 5/1992 | Blessing et al. |
| 5,180,854 A * | 1/1993 | Abatjoglou ............. C07C 45/50 568/451 |
| 5,210,318 A | 5/1993 | Briggs et al. |
| 5,237,106 A | 8/1993 | Babin et al. |
| 5,288,918 A | 2/1994 | Maher et al. |
| 5,312,996 A | 5/1994 | Packett |
| 5,360,938 A | 11/1994 | Babin et al. |
| 5,430,194 A | 7/1995 | Barner et al. |
| 5,442,107 A | 8/1995 | Beevor et al. |
| 5,449,653 A | 9/1995 | Briggs et al. |
| 5,491,266 A | 2/1996 | Babin et al. |
| 5,675,041 A | 10/1997 | Kiss et al. |
| 5,681,473 A | 10/1997 | Miller et al. |
| 5,728,893 A | 3/1998 | Becker et al. |
| 5,731,472 A | 3/1998 | Leung et al. |
| 5,731,473 A * | 3/1998 | Bryant ..................... B01J 19/18 568/451 |
| 5,741,942 A | 4/1998 | Bryant et al. |
| 5,741,944 A | 4/1998 | Bryant et al. |
| 5,929,289 A | 7/1999 | Abatjoglou et al. |
| 6,090,987 A | 7/2000 | Billig et al. |
| 6,946,580 B2 | 9/2005 | Banister et al. |
| 6,995,293 B2 | 2/2006 | Bohnen et al. |
| 2005/0085671 A1 | 4/2005 | Bohnen et al. |
| 2010/0006980 A1 | 1/2010 | Yoshinaga |

FOREIGN PATENT DOCUMENTS

| | | |
|---|---|---|
| EP | 872469 A1 | 10/1998 |
| GB | 1338225 A | 11/1973 |
| JP | 2006169131 A | 6/2006 |
| WO | 8808835 A1 | 11/1988 |
| WO | 9720792 A1 | 6/1997 |
| WO | 9720800 A1 | 6/1997 |
| WO | 2014149915 A1 | 9/2014 |

OTHER PUBLICATIONS

Abatjoglou, Organometallics, 1984, vol. 3, No. 6, p. 932-934.
Arhancet, Letters to Nature, 1989, vol. 339, p. 454-455.
Bergbreiter, J. Org. Chem. 1989, vol. 54, p. 2726-2730.
Brown, Journal of the Chemical Society, 1970, pp. 2753-2764.
Davis, Journal of Molecular Catalysis, 1987, vol. 39, p. 243-259.
Feldman, Journal of Molecular Catalysis, 1990, vol. 63, p. 213-221.
Guo, Journal of Molecular Catalysis, 1991, vol. 70, p. 363-368.
Guo, Journal of Organometallic Chemistry, 1991, vol. 403, p. 221-227.
Jongsma, Journal of Molecular Catalysis, 1993, vol. 83, p. 17-35.
Jongsma, Polymer, 1992, vol. 33, No. 1, p. 161-165.

(Continued)

*Primary Examiner* — Yong Chu
*Assistant Examiner* — Ana Z Muresan

(57) ABSTRACT

A heterocyclic nitrogen stabilizing agent is employed to reduce the rate of catalyst deactivation in a hydroformylation process.

12 Claims, No Drawings

(56) References Cited

OTHER PUBLICATIONS

Kohlpaintner, Applied Catalysis A, 2001, vol. 221, p. 219-225.
Lieto, Chemtech 1983, vol. 13, No. 1, p. 46.
Parrinello, J. Am. Chem. Soc., 1987, vol. 109, p. 7122-7127.
Rode, Journal of Catalysis, 1985, vol. 96, p. 563-573.
Rooy, Journal of Organometallic Chemistry, 1996, vol. 507, p. 69-73, XP004036309.
Toth, Catalysis Letters, 1991, vol. 8, p. 209-214.
Yan, Chemical Abstracts, 1995, vol. 125, No. 3, p. 33133 XP002043597.
Zhou, Applied Catalysis A: General, 2010, vol. 377, p. 114-120, XP026941599.
PCT/US2014/021510, International Search Report and Written Opinion with a mailing date of Jun. 12, 2014.
PCT/US2014/021510, International Preliminary Report on Patentability with a mailing date of Sep. 24, 2015.

* cited by examiner

HETEROCYCLIC AGENT AS CATALYTIC STABILIZING AGENT IN A HYDROFORMYLATION PROCESS

CROSS-REFERENCE TO RELATED APPLICATIONS

This application claims priority from provisional application Ser. No. 61/790,642, filed on Mar. 15, 2013, which is incorporated herein by reference in its entirety.

BACKGROUND OF THE INVENTION

The invention relates to the preparation of aldehydes by the hydroformylation process in which an alpha-olefin is hydroformylated with carbon monoxide and hydrogen in the presence of a triorganophosphine-modified rhodium catalyst.

U.S. Pat. No. 3,527,809, entitled "Hydroformylation Process" by R. L. Pruett and J. A. Smith, discloses a significant development in hydroformylation of alpha-olefins to produce aldehydes at high yields at low temperatures and pressures, and with excellent catalyst stability. When the alpha-olefin contains 3 or more carbon atoms, the process produces aldehyde mixtures containing a high normal to iso- (or branched-chain) isomer ratio. The process employs certain rhodium complex compounds to effectively catalyze, under a defined set of variables in the presence of select triorganophosphorus ligands, the hydroformylation of olefins with hydrogen and carbon monoxide. The variables include (1) the rhodium complex catalyst, (2) the olefin feed, (3) the triorganophosphorus ligand and its concentration, (4) a relatively low temperature range, (5) a relatively low total hydrogen and carbon monoxide pressure, and (6) a limitation on the partial pressure exerted by carbon monoxide.

Among the catalysts described in the aforesaid US patent are compounds containing rhodium in complex combination with the carbon monoxide and triarylphosphorus ligands, in particular triarylphosphine ligands exemplified by triphenylphosphine (TPP). A typical active catalytic species is rhodium hydridocarbonyltris (triphenylphosphine) which has the formula $RhH(CO)(P(C_6H_5)_3)_3$. The process uses an excess of the triorganophosphorus ligand.

It is known that despite efforts to prevent it, catalyst activity slowly declines with time. It has been observed that under harsh conditions, the phosphine ligand undergoes side reactions such as aryl exchange between phosphines as well as incorporation of olefin to form alkyl moieties with loss of an aryl group (Abatjoglou, et al., *Organometallics*, 1984, 3, 923). This alters the make-up of the phosphines present in the system which may form catalyst inhibitors (U.S. Pat. Nos. 4,260,828 and 4,283,304). In aqueous systems utilizing ionic ligands, such an exchange of groups on the phosphorus moiety can result in the loss of the ionic group (Kohlpaintner, et al; *Applied Catalysis A* 2001, 219), which negatively impacts reactivity and renders the phosphine less ionic which may promote rhodium loss in these biphasic reaction schemes.

U.S. Pat. No. 4,277,627 teaches about several routes of catalyst deactivation including intrinsic deactivation. Operating conditions are specifically stated that minimize the loss of activity with these phosphine-based catalysts. U.S. Pat. No. 4,605,780 teaches that one of the main sources of deactivation of triarylphosphine-based catalysts is the formation of alkyldiphenylphosphines due to alkyl and aryl substituent exchange on the phosphine. U.S. Pat. No. 4,605,780, U.S. Pat. No. 4,710,587 and U.S. Pat. No. 6,946,580 teach off-line processes to reduce the level of these catalyst inhibitors but do not teach how to prevent them. These off-line processes are costly, as production is lost while the catalyst is regenerated.

U.S. Pat. No. 5,237,106, U.S. Pat. No. 5,180,854, and U.S. Pat. No. 4,861,918 teach yet another set of techniques to reactivate Rh-triarylphosphine catalysts using reagents in off-line processing. While effective in recovering much of the catalytic activity, these do not prevent the initial deactivation or future deactivation.

Other examples of catalyst activity loss have been reported for phosphite and polyphosphite-based catalysts. U.S. Pat. No. 6,090,987 discusses the addition of a diene additive to mitigate rhodium deactivation via clustering. U.S. Pat. No. 5,731,472 discusses the use of heterocyclic nitrogen compounds to prevent clustering (as well as the use of acid-removal technologies) in "hydrolyzable" phosphite-based hydroformylation catalysts. U.S. Pat. No. 5,741,942 and U.S. Pat. No. 5,741,944 discuss hydrolysis-based catalyst issues which include the addition of various amine additives which appear to help stabilize these "hydrolyzable" organophosphorus ligands (i.e., phosphites and polyphosphites). However, the type of catalyst deactivation found with these types of phosphite ligands is different than observed with the phosphine-based catalysts which, generally, do not undergo hydrolysis reactions. For example, the hydrolysis-based inhibitors derived from the breakdown of phosphites can lead to rhodium-black (Rh-metal colloids, etc.) and those inhibitors are different from the phosphido-bridged dimers that are derived from phosphine catalysts. For example, U.S. Pat. No. 5,675,041 teaches that Rh-TPP deactivation typically is associated with color formation due to the phosphido-bridged dimers. Phosphite-based activity loss generally does not involve such a color change (e.g., U.S. Pat. No. 5,288,918) or involves Rh loss, possibly with a black/grey appearance.

It would be desirable to have a continuous catalyst activity maintenance process as a means to reduce or prevent the loss of activity in Rh-triorganophosphine hydroformylation catalysts, which process would not involve an off-line removal of the catalyst from the reaction zone and which would maintain high productivity at minimal capital or operating expense.

SUMMARY OF THE INVENTION

Surprisingly, adding a small amount of a heterocyclic amine compound reduces the rate of catalyst activity loss by (1) reducing phosphine ligand degradation and (2) reducing the rate of the intrinsic deactivation process. The ligand degradation (alkyl and aryl exchange on the phosphine) has been observed before but no means to mitigate this undesired reaction has been reported.

DETAILED DESCRIPTION OF THE INVENTION

The disclosed process comprises contacting CO, $H_2$, a heterocyclic nitrogen stabilizing agent and at least one olefin under hydroformylation conditions sufficient to form at least one aldehyde product in the presence of a catalyst comprising, as components, a transition metal and a triorganophosphine ligand.

All references to the Periodic Table of the Elements and the various groups therein are to the version published in the CRC Handbook of Chemistry and Physics, 72nd Ed. (1991-1992) CRC Press, at page I-10.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible sub-ranges that are included in that range. For example, the range from 1 to 100 is intended to convey from 1.01 to 100, from 1 to 99.99, from 1.01 to 99.99, from 40 to 60, from 1 to 55, etc. Also herein, the recitations of numerical ranges and/or numerical values, including such recitations in the claims, can be read to include the term "about." In such instances the term "about" refers to numerical ranges and/or numerical values that are substantially the same as those recited herein.

As used herein, the term "ppmw" means part per million by weight.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds that can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxyalkyl, aminoalkyl, in which the number of carbons can range from 1 to 20 or more, preferably from 1 to 12, as well as hydroxy and amino. The permissible substituents can be one or more and the same or different for appropriate organic compounds. This invention is not intended to be limited in any manner by the permissible substituents of organic compounds.

As used herein, the term "hydroformylation" is contemplated to include, but not limited to, all permissible asymmetric and non-asymmetric hydroformylation processes that involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes.

The terms "reaction fluid," "reaction medium" and "catalyst solution" are used interchangeably herein, and may include, but are not limited to, a mixture comprising: (a) a metal-organophosphorus ligand complex catalyst, (b) free organophosphorus ligand, (c) aldehyde product formed in the reaction, (d) unreacted reactants, (e) a solvent for said metal-organophosphorus ligand complex catalyst and said free organophosphorus ligand, and, optionally, (f) one or more phosphorus acidic compounds formed in the reaction (which may be homogeneous or heterogeneous, and these compounds include those adhered to process equipment surfaces) and (g) organophosphorus ligand decomposition products such as the corresponding oxide. The reaction fluid can encompass, but is not limited to, (a) a fluid in a reaction zone, (b) a fluid stream on its way to a separation zone, (c) a fluid in a separation zone, (d) a recycle stream, (e) a fluid withdrawn from a reaction zone or separation zone, (f) a withdrawn fluid being treated with an aqueous buffer solution, (g) a treated fluid returned to a reaction zone or separation zone, (h) a fluid in an external cooler, and (i) ligand decomposition products and their salts.

Hydrogen ($H_2$) and carbon monoxide may be obtained from any suitable source, including petroleum cracking and refinery operations. Syngas mixtures are a preferred source of hydrogen and CO.

Syngas (from synthesis gas) is the name given to a gas mixture that contains varying amounts of CO and $H_2$. Production methods are well known. Hydrogen and CO typically are the main components of syngas, but syngas may contain $CO_2$ and inert gases such as $N_2$ and Ar. The ratio of $H_2$ to CO varies greatly but generally ranges from 1:100 to 100:1 and preferably between 1:10 and 10:1. Syngas is commercially available and is often used as a fuel source or as an intermediate for the production of other chemicals. The most preferred $H_2$:CO ratio for chemical production is between 3:1 and 1:3 and usually is targeted to be between about 1:2 and 2:1 for most hydroformylation applications.

The substituted or unsubstituted olefinic unsaturated reactants that may be employed in the hydroformylation process include both optically active (prochiral and chiral) and non-optically active (achiral) olefinic unsaturated compounds containing from 2 to 40, preferably 2 to 20, more preferably 3 to 16 carbon atoms. These compounds are described in detail in US 2010/006980, except that for the purposes of this invention the olefinic reactant is halogen-free. Such olefinic unsaturated compounds can be terminally or internally unsaturated and be of straight-chain, branched chain or cyclic structures, as well as olefin mixtures, such as obtained from the oligomerization of propene, butene, isobutene, etc. (such as so called dimeric, trimeric or tetrameric propylene and the like, as disclosed, for example, in U.S. Pat. Nos. 4,518,809 and 4,528,403).

Prochiral and chiral olefins useful in the asymmetric hydroformylation that can be employed to produce enantiomeric aldehyde mixtures include those represented by the formula:

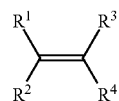

I wherein $R^1$, $R^2$, $R^3$ and $R^4$ are the same or different (provided that $R^1$ is different from $R^2$ or $R^3$ is different from $R^4$) and are selected from hydrogen; alkyl; substituted alkyl, said substitution being selected from dialkylamino such as benzylamino and dibenzylamino, alkoxy such as methoxy and ethoxy, acyloxy such as acetoxy, nitro, nitrile, thio, carbonyl, carboxamide, carboxaldehyde, carboxyl, and carboxylic ester; aryl including phenyl; substituted aryl including phenyl, said substitution being selected from alkyl, amino including alkylamino and dialkylamino such as benzylamino and dibenzylamino, hydroxy, alkoxy such as methoxy and ethoxy, acyloxy such as acetoxy, nitrile, nitro, carboxyl, carboxaldehyde, carboxylic ester, carbonyl, and thio; acyloxy such as acetoxy; alkoxy such as methoxy and ethoxy; amino including alkylamino and dialkylamino such as benzylamino and dibenzylamino; acylamino and diacylamino such as acetylbenzylamino and diacetylamino; nitro; carbonyl; nitrile; carboxyl; carboxamide; carboxaldehyde; carboxylic ester; and alkylmercapto such as methylmercapto. It is understood that the prochiral and chiral olefins of this definition also include molecules of the above general formula where the R groups are connected to form ring compounds, e.g., 3-methyl-1-cyclohexene, and the like.

Illustrative optically active or prochiral olefinic compounds useful in asymmetric hydroformylation are described, for example, in U.S. Pat. Nos. 4,329,507, 5,360,938 and 5,491,266.

A solvent advantageously is employed in the hydroformylation process. Any suitable solvent that does not unduly interfere with the hydroformylation process can be used. By way of illustration, suitable solvents for rhodium catalyzed hydroformylation processes include those disclosed, for example, in U.S. Pat. Nos. 3,527,809; 4,148,830; 5,312,996; and 5,929,289. Non-limiting examples of suitable solvents include saturated hydrocarbons (alkanes), aromatic hydrocarbons, water, ethers, aldehydes, ketones, nitriles, alcohols, esters, and aldehyde condensation products. Specific examples of solvents include: tetraglyme, pentanes, cyclohexane, heptanes, benzene, xylene, toluene, diethyl ether, tetrahydrofuran, butyraldehyde, and benzonitrile. The organic solvent may also contain dissolved water up to the saturation limit. Illustrative preferred solvents include ketones (e.g., acetone and methylethyl ketone), esters (e.g., ethyl acetate, di-2-ethylhexyl phthalate, 2,2,4-trimethyl-1,3-pentanediol monoisobutyrate), hydrocarbons (e.g., toluene), nitrohydrocarbons (e.g., nitrobenzene), ethers (e.g., tetrahydrofuran (THF)) and sulfolane. In rhodium catalyzed hydroformylation processes, it may be preferred to employ, as a primary solvent, aldehyde compounds corresponding to the aldehyde products desired to be produced and/or higher boiling aldehyde liquid condensation by-products, for example, as might be produced in situ during the hydroformylation process, as described for example in U.S. Pat. No. 4,148,380 and U.S. Pat. No. 4,247,486. The primary solvent will normally eventually comprise both aldehyde products and higher boiling aldehyde liquid condensation by-products ("heavies"), due to the nature of the continuous process. The amount of solvent is not especially critical and need only be sufficient to provide the reaction medium with the desired amount of transition metal concentration. Typically, the amount of solvent ranges from about 5 percent to about 95 percent by weight, based on the total weight of the reaction fluid. Mixtures of solvents may be employed.

Illustrative metal-organophosphorus ligand complexes employable in such hydroformylation reactions include metal-organophosphorus ligand complex catalysts. These catalysts, as well as methods for their preparation, are well known in the art and include those disclosed in the patents mentioned herein. In general, such catalysts may be preformed or formed in situ and comprise metal in complex combination with an organophosphorus ligand, carbon monoxide and optionally hydrogen. The ligand complex species may be present in mononuclear, dinuclear and/or higher nuclearity forms. However, the exact structure of the catalyst is not known.

The metal-organophosphorus ligand complex catalyst can be optically active or non-optically active. The metals can include Group 8, 9 and 10 metals selected from rhodium (Rh), cobalt (Co), iridium (Ir), ruthenium (Ru), iron (Fe), nickel (Ni), palladium (Pd), platinum (Pt), osmium (Os) and mixtures thereof, with the preferred metals being rhodium, cobalt, iridium and ruthenium, more preferably rhodium, cobalt and ruthenium, especially rhodium. Mixtures of these metals may be used. The permissible organophosphorus ligands that make up the metal-organophosphorus ligand complexes and free organophosphorus ligand include mono-, di-, tri- and higher polyorganophosphorus ligands. Mixtures of ligands may be employed in the metal-organophosphorus ligand complex catalyst and/or free ligand, and such mixtures may be the same or different.

The organophosphorus compounds that may serve as the ligand of the metal-organophosphorus ligand complex catalyst and/or free ligand may be of the achiral (optically inactive) or chiral (optically active) type and are well known in the art. Achiral organophosphorus ligands are preferred.

The triorganophosphine employable in the process of this disclosure comprises any organic compound comprising one phosphorus atom covalently bonded to three alkyl, aryl or arylalkyl radicals, or combinations thereof. A mixture of triorganophosphine ligands may also be employed. Representative organomonophosphines include those having the formula IV and organodiphosphines shown in formula V:

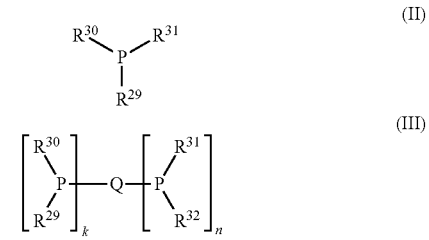

wherein where Q represents a polyvalent organic bridging group, n and k independently are from 0 to 3 with k+n being at least 2, and each $R^{29}$, $R^{30}$, $R^{31}$ and $R^{32}$ may be the same or different and represent a substituted or unsubstituted alkyl or aryl radical containing from 4 to 40 carbon atoms or greater. Illustrative substituent groups that may be present on the aryl radicals, include e.g., alkyl radicals, alkoxy radicals, silyl radicals such as —Si$(R^{34})_3$; amino radicals such as —N$(R^{34})_2$; acyl radicals such as —C(O)$R^{34}$; carboxy radicals such as —C(O)O$R^{34}$; acyloxy radicals such as —OC(O)$R^{34}$; amido radicals such as —C(O)N$(R^{34})_2$ and —N$(R^{34})$C(O)$R^{34}$; sulfonyl radicals such as —SO$_2R^{34}$; ether radicals such as —O$R_3^4$; thionyl ether radicals such as —S$R^{34}$ as well as nitro, cyano, trifluoromethyl and hydroxy radicals, and the like, wherein each $R^{34}$ individually represents the same or different substituted or unsubstituted monovalent hydrocarbon radical having the same meaning as defined for $R^1$, $R^2$ and $R^3$ above, with the proviso that in amino substituents such as —N$(R^{34})_2$, each $R^{34}$ taken together can also represent a divalent bridging group that forms a heterocyclic radical with the nitrogen atom and in amido substituents such as C(O)N$(R^{34})_2$ and —N$(R^{34})$C(O)

$R^{34}$ each —$R^{34}$ bonded to N can also be hydrogen. Illustrative aryl radicals represented by $R^{29}$, $R^{30}$ and $R^{31}$ include e.g., phenyl, naphthyl, diphenyl, fluorophenyl, difluorophenyl, benzoyloxyphenyl, carboethoxyphenyl, acetylphenyl, ethoxyphenyl, phenoxyphenyl, hydroxyphenyl, carboxyphenyl, trifluoromethylphenyl, methoxyethylphenyl, acetamidophenyl, dimethylcarbamoylphenyl, tolyl, xylyl, and the like.

The ligand may be an ionic organophosphine ligand capable of forming a coordination complex with the rhodium. A wide variety of such ionic organophosphine ligands potentially can be used. Suitable ionic organophosphine ligands that may be employed are those having the general formulae (IV) and (V):

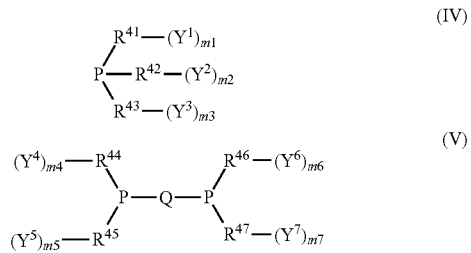

where $R^{41}$, $R^{42}$ and $R^{43}$ of formula (IV) and $R^{44}$, $R^{45}$, $R^{46}$ and, $R^{47}$ of formula (V) each individually represent a hydrocarbon radical containing from 1 to 30 carbon atoms selected from the group consisting of alkyl, aryl, alkaryl, aralkyl, and cycloalkyl radicals, where Q in formula (V) represents a divalent organic bridging group and where $Y^1$, $Y^2$ and $Y^3$ of formula (IV) and $Y^4$, $Y^5$, $Y^6$, and $Y^7$ of formula V) are substituted on the hydrocarbon radical and each individually represents an ionic radical of overall neutral charge selected from the group consisting of:

—$SO_3M$ wherein M represents inorganic or organic cationic atoms or radicals (but not exclusively hydrogen) or, —$PO_3M$ wherein M represents inorganic or organic cationic atoms (but not exclusively hydrogen) or, —$NR_3X'$ wherein each R represents a hydrocarbon radical containing from 1 to 30 carbon atoms selected from the class consisting of alkyl, aryl, alkaryl, aralkyl and cycloalkyl radicals, and X' represents inorganic or organic anionic atoms or, —$CO_2M$ wherein M represents inorganic or organic cationic atoms (but not exclusively hydrogen), wherein m1, m2 and m3 of formula (IV) and m4, m5, m6, and m7 of formula (2) are integers which can be the same or different and which can range from 0 to 5. At least one of m1, m2 and m3 and at least one of m4, m5, m6 and m7 cannot be zero (0), i.e., must be equal to or greater than 1. The integers m1 through m7 indicate the number of ionic radicals of overall neutral charge substituted on each hydrocarbon radical.

The hydrocarbon radicals, $R^{29}$, $R^{30}$ $R^{31}$ and $R^{32}$ of Formulas (II) and (III), $R^{43}$ $R^{41}$, $R^{42}$ and $R^{43}$ of formula (IV) and $R^{44}$, $R^{45}$, $R^{46}$, and $R^{47}$ of formula (V) preferably contain from 1 to 18 carbon atoms. Hydrocarbon radicals containing from 1 to 12 carbon atoms are more preferred. Such hydrocarbon radicals include those e.g., selected from the group consisting of alkyl, aryl, alkaryl, aralkyl and cycloalkyl. Illustrative hydrocarbon radicals are e.g., methyl, ethyl, propyl, butyl, hexyl, cyclohexyl, phenyl and the like. Most preferably at least one of $R^{41}$, $R^{42}$ and $R^{43}$ in formula (IV) and at least one of $R^{44}$, $R^{45}$, $R^{46}$ and $R^{47}$ in formula (V) is a phenyl radical. Such hydrocarbon radicals may contain one or more substitutents provided that they do not unduly adversely affect the use of the ligand and this invention. Suitable substitutents include straight and branched chain alkyl groups, preferably of 1 to 4 carbon atoms, alkoxy groups, hydroxy, cyano, nitro and amino groups and the like. More preferably at least two, and most preferably three of $R^{41}$, $R^{42}$ and $R^{43}$ in formula (IV) are phenyl groups and at least three and most preferably four of $R^{44}$, $R^{45}$, $R^{46}$ and $R^{47}$ in formula (V) are phenyl radicals.

The organic divalent bridging group represented by Q in the above formulas is a polyvalent radical (preferably divalent) containing from 1 to 30 carbon atoms selected from the group consisting of hydrocarbon radicals, oxygen containing hydrocarbon radicals (i.e., hydrocarbon radicals interrupted with an oxygen atom), sulfur containing hydrocarbon radicals (i.e., hydrocarbon radicals interrupted with a sulfur atom) and nitrogen containing hydrocarbon atoms (i.e., hydrocarbon radicals interrupted with a nitrogen atom). Preferably such radicals contain from 1 to 16 and more preferably from 1 to 12 carbon atoms. Illustrative divalent hydrocarbon radicals include alkylene radicals (e.g., methylene (—$CH_2$—), ethylene, propylene, isopropylene, butylene, 1,2-dimethylethylene, t-butylene, neopentylene, 2-methylpropylene, hexylene, 2-ethylhexylene, dodecylene, eicosylene, and the like); arylene radicals (e.g., phenylene, substituted phenylene, diphenylene, substituted diphenylene, and the like); as well as alkylene containing arylene radicals (e.g., methylenephenylene (—$CH_2C_6H_4$—), (ethylenephenylethylene (—$CH_2C_6H_4$—$C_2H_4$—), phenylenepropylphenylene (—$C_6H_4C(CH_3)_2C_6H_4$—), methylenediphenylmethylene (—$CH_2C_6H_4C_6H_4CH_2$—), and the like; and alkylidene radicals (e.g., ethylidene (—CH=CH—), and the like). Illustrative oxygen containing hydrocarbon radicals include alkyleneoxyalkylene radicals (e.g., ethyleneoxymethylene (—$C_2H_4OCH_2$—), propyleneoxymethylene (—$C_3H_6OCH_2$—), ethyleneoxyethylene (—$C_2H_4OC_2H_4$—), 1,2-bis(ethyleneoxy)ethane (—$C_2H_4OC_2H_4OC_2H_4$—), propyleneoxypropylene (—$C_3H_6OC_3H_6$—) and the like); aryleneoxyalkylene radicals (e.g., phenyleneoxymethylene (—$C_6H_4OCH_2$—), and the like); and the like. Illustrative sulfur or thio containing hydrocarbon radicals include alkylenethioalkylene radicals (e.g., ethlenethioethylene (—$C_2H_4SC_2H_4$—), 1,2-bis(ethylenethio)ethane (—$C_2H_4SC_2H_4SC_2H_4$—), propylenethiomethylene (—$C_3H_6SCH_2$—), propylenethiopropylene (—$C_3H_6SC_3H_6$—), and the like); arylenethioalkylene radicals (e.g., phenylenethiomethylene (—$C_3H_6S$—$CH_2$—)$_9$ and the like); and the like. Illustrative amino containing hydrocarbon radicals include alkyleneaminoalkylene radicals (e.g., methyleneaminomethylethylene (—$CH_2N(CH_3)$ $C_2H_4$—), ethyleneneaminomethylethylene (—$C_2H_4N(CH_3)$ $C_2H_4$—), bis(ethyleneaminomethyl) ethane (—$C_2H_4N$ $(CH_3)C_2H_4N(CH_3)C_2H_4$—), propyleneaminomethylpropylene (—$C_3H_6N(CH_3)C_3H_6$—) and the like. Most preferably Q is a divalent hydrocarbon radical, especially a divalent alkylene radical containing from 2 to 8 carbon atoms. The values of k and n in Formula III range from 0 to 3 with k+n being at least 2.

Particularly suitable ionic organophosphine ligands are the ionic triarylphosphines and, in particular, the salts of sulfonated and carboxylated triarylphosphines, as, for example, are described in U.S. Pat. Nos. 4,248,802; 4,399, 312; 4,668,824; 4,716,250, 4,731,486 and 4,929,767. Preferred among this group are the salts of monosulfonated and of trisulfonated triphenylphosphines, and the salts of monocarboxylated and of tricarboxylated triphenylphosphine.

Another suitable class of ionic organophosphines are ionic bisdiarylphosphines such as bisdiphenylphosphinoethane monosulfonate salts. Mixtures of suitable ionic phosphine ligands also can be employed.

Such triarylphosphines may be found described in greater detail, for example, in U.S. Pat. No. 3,527,809, the disclosure of which is incorporated herein by reference. Illustrative triarylphosphine ligands are triphenylphosphine, trinaphthylphine, tritolylphosphine, tri(p-biphenyl)phosphine, tri(p-methoxyphenyl)phosphine, tri(m-chlorophenyl)-phosphine, p-N,N-dimethylaminophenyl bis-phenyl phosphine, and the like. Triphenyl phosphine, i.e., the compound of Formula II wherein each $R^{29}$, $R^{30}$ and $R^{31}$ is phenyl, is an example of a preferred organomonophosphine ligand. As pointed out previously, the reaction is effected in a liquid body containing excess, free triarylphosphine.

The preferred catalyst of this invention comprises rhodium complexed with carbon monoxide and a triarylphosphine ligand. The most desirable catalyst is free of metal-bound halogens such as chlorine, and contains hydrogen, carbon monoxide and triaryl phosphine complexed with rhodium metal to produce a catalyst soluble in the aforementioned liquid body and stable under the conditions of the reaction.

Rhodium is preferably introduced into the liquid body as a preformed catalyst, e.g., a stable crystalline solid, rhodium hydridocarbonyl-tris(triphenyl phosphine), $RhH(CO)(PPh_3)_3$. The rhodium can be introduced to the liquid body as a precursor form which is converted in situ into the catalyst. Examples of such precursor form are rhodium carbonyl triphenylphosphine acetylacetonate, $Rh_2O_3$, $Rh_4(CO)_{12}$, $Rh_6(CO)_{16}$, and rhodium dicarbonyl acetylacetonate. Both the catalyst compounds that will provide active species in the reaction medium and their preparation are known in the art; see, e.g., Brown et al., *Journal of the Chemical Society*, 1970, pp. 2753-2764.

In ultimate terms the rhodium concentration in the liquid body can range from about 25 ppm to about 1200 ppm of rhodium calculated as free metal, and the triarylphosphine is present in the range of about 0.5 percent to about 30 percent by weight, based on the weight of the total reaction mixture, and in an amount sufficient to provide at least 10 moles of free triarylphosphine per mole of rhodium.

In general the optimum catalyst concentration depends on the concentration of the alpha-olefin, such as propylene. For example, the higher the propylene concentration the lower usually will be the catalyst concentration that can be used to achieve a given conversion rate to aldehyde products in a given size of reactor. Recognizing that partial pressures and concentration are related, the use of higher propylene partial pressure leads to an increased proportion of propylene in the "off gas" from the liquid body. Since it may be necessary to purge part of the gas stream from the product recovery zone before recycle to the liquid body in order to remove a portion of the propane which may be present, the higher the propylene content of the "off gas" is, the more propylene that will be lost in the propane purge stream. Thus it is necessary to balance the economic value of the propylene lost in the propane purge stream against the capital savings associated with lower catalyst concentration.

The metal-organophosphorus ligand complex catalysts may be in homogeneous or heterogeneous form. For instance, preformed rhodium hydrido-carbonyl-organophosphorus ligand catalysts may be prepared and introduced into a hydroformylation reaction mixture. More preferably, the rhodium-organophosphorus ligand complex catalysts can be derived from a rhodium catalyst precursor that may be introduced into the reaction medium for in situ formation of the active catalyst. For example, rhodium catalyst precursors such as rhodium dicarbonyl acetylacetonate, $Rh_2O_3$, $Rh_4(CO)_{12}$, $Rh_6(CO)_{16}$, $Rh(NO_3)_3$ and the like may be introduced into the reaction mixture along with the organophosphorus ligand for the in situ formation of the active catalyst. In a preferred embodiment, rhodium dicarbonyl acetylacetonate is employed as a rhodium precursor and reacted in the presence of a solvent with the organophosphorus ligand to form a catalytic rhodium-organophosphorus ligand complex precursor that is introduced into the reactor along with excess (free) organophosphorus ligand for the in situ formation of the active catalyst. In any event, it is sufficient that carbon monoxide, hydrogen and the organophosphorus ligand are all ligands that are capable of being complexed with the metal and that an active metal-organophosphorus ligand catalyst is present in the reaction mixture under the conditions used in the hydroformylation reaction. Carbonyl and organophosphorus ligands may be complexed to the rhodium either prior to or in situ during the hydroformylation process.

By way of illustration, a preferred catalyst precursor composition consists essentially of a solubilized rhodium carbonyl organophosphine ligand complex precursor, a solvent and, optionally, free organophosphine ligand. The preferred catalyst precursor composition can be prepared by forming a solution of rhodium dicarbonyl acetylacetonate, an organic solvent and a organophosphine ligand. The organophosphorus ligand readily replaces one of the carbonyl ligands of the rhodium acetylacetonate complex precursor as witnessed by the evolution of carbon monoxide gas.

Accordingly, the metal-organophosphorus ligand complex catalyst advantageously comprise the metal complexed with carbon monoxide and an organophosphorus ligand, said ligand being bonded (complexed) to the metal in a chelated and/or non-chelated fashion.

Mixtures of catalysts can be employed. The amount of metal-organophosphorus ligand complex catalyst present in the reaction fluid need only be that minimum amount necessary to provide the given metal concentration desired to be employed and that will furnish the basis for at least the catalytic amount of metal necessary to catalyze the particular hydroformylation process involved such as disclosed, for example, in the above-mentioned patents. In general, catalytic metal, e.g., rhodium, concentrations in the range of from 10 ppmw to 1000 ppmw, calculated as free metal in the reaction medium, should be sufficient for most processes, while it is generally preferred to employ from 10 to 500 ppmw of metal, and more preferably from 25 to 350 ppmw of metal.

In addition to the metal-organophosphorus ligand complex catalyst, free organophosphorus ligand (i.e., ligand that is not complexed with the metal) may also be present in the reaction medium. The significance of free ligand is taught in U.S. Pat. No. 3,527,809, GB 1,338,225, and Brown et al., supra., pages 2759 and 2761. The free organophosphorus ligand may correspond to any of the above-defined organophosphorus ligands discussed above. It is preferred that the free organophosphorus ligand be the same as the organophosphorus ligand of the metal-organophosphorus ligand complex catalyst employed. However, such ligands need not be the same in any given process. The hydroformylation process of this invention may involve from 0.1 moles or less to 1000 moles or higher of free organophosphorus ligand per mole of metal in the reaction medium. Preferably, the hydroformylation process is carried out in the presence of from 1 to 30 weight percent organophosphorus ligand, based on the weight of the reaction medium. More preferably, for arylphosphines, from 3 to 15 weight percent of arylphosphine ligand are employed. Said amounts of organophosphorus ligand are the sum of both the amount of organophosphorus ligand that is bound (complexed) to the metal present and the amount of free organophosphorus ligand present. If desired, additional organophosphorus ligand can be supplied to the reaction medium of the hydroformylation process at any time and in any suitable manner, e.g., to maintain a predetermined level of free ligand in the reaction medium.

In one embodiment, the rhodium catalyst may be impregnated onto any solid support, such as inorganic oxides, (i.e., alumina, silica, titania, or zirconia) carbon, or ion exchange resins, supported on, or intercalated inside the pores of, a zeolite, glass or clay, or may also be dissolved in a liquid film coating the pores of said zeolite or glass. Such zeolite-supported catalysts are particularly advantageous for producing one or more regioisomeric aldehydes in high selectivity, as determined by the pore size of the zeolite.

The solid catalyst thus formed may still be complexed with one or more of the ligands defined above. Descriptions of such solid catalysts may be found in for example: *J. Mol. Cat.* 1991, 70, 363-368; *Catal. Lett.* 1991, 8, 209-214; *J. Organomet. Chem.* 1991, 403, 221-227; *Nature*, 1989, 339, 454-455; *J. Catal.* 1985, 96, 563-573; *J. Mol. Cat.* 1987, 39, 243-259. The catalyst may be attached to a thin film or membrane support, such as cellulose acetate or polyphenylenesulfone, as described in, for example, *J. Mol. Cat.*, 1990, 63, 213-221. The catalyst may be attached to an insoluble polymeric support through an organophosphorus-containing ligand, such as a phosphine, incorporated into the polymer. Descriptions of polymer-supported catalysts may be found in for example: *J. Mol. Cat.*, 1993, 83, 17-35; *Chemtech* 1983, 46; *J. Am. Chem. Soc.*, 1987, 109, 7122-7127. In another embodiment, the catalyst may be supported on a polymer that, by the nature of its molecular weight, is soluble in the reaction medium at elevated temperatures, but precipitates upon cooling, thus facilitating catalyst separation from the reaction mixture. Such "soluble" polymer-supported catalysts are described in for example: *Polymer*, 1992, 33, 161; *J. Org. Chem.* 1989, 54, 2726-2730.

A slow loss in catalytic activity has been observed when phosphine ligand promoted metal catalysts are employed in processes that involve harsh conditions, such as recovery of the aldehyde via a vaporizer-separator. Surprisingly, the rate of activity loss is reduced when an heterocyclic nitrogen stabilizing agent is added to the hydroformylation reaction fluid. The agent can be added to the fluid in any suitable manner, e.g., continuously or intermittently.

Without wishing to be bound to any exact theory it is believed that the encountered slow loss in catalytic activity of triarylphosphine-promoted metal hydroformylation catalysts is due at least in part to the harsh conditions employed in the separation and recovery of the aldehyde product from its reaction product fluid. For instance, it has been found that when a triarylphosphine-promoted rhodium catalyst is placed under harsh conditions, such as high temperature and low carbon monoxide partial pressure, that are common in a vaporizer, then the catalyst deactivates at an accelerated pace, due most likely to the formation of an inactive or less active rhodium species, which may also be susceptible to precipitation under prolonged exposure to such harsh conditions. This is consistent with the view that the active catalyst, which under hydroformylation conditions is believed to comprise a complex of rhodium, triarylphosphine, carbon monoxide and hydrogen, loses at least some of its coordinated carbon monoxide ligand during harsh conditions such as exist during separation, e.g., vaporization, which provides a route for the formation of such catalytically inactive or less active rhodium species.

By way of further explanation it is believed the heterocyclic nitrogen stabilizing agent serves as a replacement ligand for the lost carbon monoxide ligand thereby forming a neutral intermediate metal, e.g., rhodium, species comprising a complex of metal, triarylphosphine, the heterocyclic nitrogen stabilizing agent and hydrogen during such separation under harsh conditions, thereby preventing or minimizing the formation of any such above-mentioned catalytically inactive or less active rhodium species. It is further theorized that the maintenance of catalytic activity, or the minimization of its deactivation, throughout the course of such continuous liquid recycle hydroformylation is due to regeneration of the active catalyst from said neutral intermediate rhodium species in the reactor (i.e., hydroformylation reaction zone) of the particular hydroformylation process involved. It is also believed that under the higher syn gas pressure hydroformylation conditions in the reactor, the active catalyst complex comprising metal, e.g., rhodium, triarylphosphine, carbon monoxide and hydrogen, is regenerated as a result of some of the carbon monoxide in the reactant syn gas replacing the heterocyclic nitrogen ligand of the recycled neutral intermediate rhodium species. That is to say, carbon monoxide, having a stronger ligand affinity for rhodium, replaces the more weakly bonded heterocyclic nitrogen ligand of the recycled neutral intermediate rhodium species that was formed during vaporization separation as mentioned above, thereby reforming the active catalyst in the hydroformylation reaction zone. It is key to note that the heterocyclic nitrogen stabilizing agent is sufficiently weakly bound as to be readily displaced by CO, so that its presence does not impact the hydroformylation kinetics, yet the heterocyclic nitrogen stabilizing agent is strong enough to bind to the Rh in the harsh vaporizer environment. Regardless of the specific mechanism involved in the formation of an intermediate rhodium species and/or the regeneration of active catalyst, it should be sufficient to note that the use of a heterocyclic nitrogen stabilizing agent in accordance with this invention is an excellent means for preventing or minimizing catalytic activity loss of triarylphosphine-promoted metal hydroformylation catalysts due to harsh conditions.

A means for preventing or minimizing such catalyst deactivation and/or precipitation comprises carrying out the portion of the hydroformylation process that involves harsh conditions such as the separation, e.g., vaporization, procedure of the hydroformylation process in the presence of one or more heterocyclic nitrogen stabilizing agents.

The free heterocyclic nitrogen compounds which are employable herein as heterocyclic nitrogen stabilizing agents are well known compounds, as are methods for their preparation. In many instances they are readily available commercially. While it may be preferred to employ only one free heterocyclic nitrogen compound at a time in any given hydroformylation process, if desired, mixtures of two or more different free heterocyclic nitrogen compounds may also be employed in any given process. Suitable substituted and unsubstituted heterocyclic nitrogen compounds include those permissible substituted and unsubstituted heterocyclic nitrogen compounds described in Kirk-Othmer, "Encyclopedia of Chemical Technology," Fourth Edition, 1996, the pertinent portions of which are incorporated herein by reference.

Illustrative the heterocyclic nitrogen stabilizing agent compounds include the following diazoles:

(a) imidazoles represented by the formula:

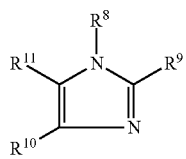

(IX)

(b) pyrazoles represented by the formula:

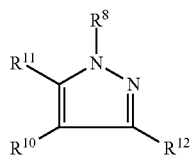

(X)

and (c) indazoles represented by the formula:

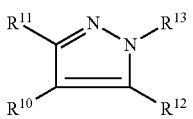

(XI)

wherein in Formulas (IX), (X) and (XI) above, $R^8$, $R^9$, $R^{10}$, $R^{11}$, $R^{12}$ and $R^{13}$ are identical or different and each represents a hydrogen atom or a monovalent substituent, with the proviso that, in one embodiment of the invention, $R^8$ and $R^9$ should not both be monovalent hydrocarbon radicals at the same time. The adjacent substituents $R^8$ and $R^{11}$, or $R^8$ and $R^9$, or $R^{10}$ and $R^{11}$, or $R^{10}$ and $R^{12}$, or $R^{12}$ and $R^{13}$ may optionally be taken together to form a substituted or unsubstituted divalent radical which together with the two atoms of the formula to which said adjacent substituents are bonded form a cyclic ring.

The monovalent $R^8$ to $R^{13}$ substituents in Formulas (IX), (X) and (XI) can be any substituent that does not unduly adversely affect the purpose and process of the invention. Examples of such monovalent substituents include hydroxy, cyano, nitro, trifluoromethyl and substituted or unsubstituted radicals containing from 1 to 30 carbon atoms selected from the group consisting, acyl, acyloxy carbonyloxy, oxycarbonyl, silyl, alkoxy, aryloxy, cycloalkoxy, alkyl, aryl, alkaryl, aralkyl, and alicyclic radicals.

More specifically illustrative monovalent substituents containing from 1 to 30 carbon atoms include e.g., primary, secondary and tertiary alkyl radicals such as methyl, ethyl, n-propyl, isopropyl, butyl, sec-butyl, t-butyl, neo-pentyl, n-hexyl, arnyl, sec-amyl, t-amyl, iso-octyl, decyl, octadecyl, and the like; aryl radicals such as phenyl, naphthyl and the like; aralkyl radicals such as benzyl, phenylethyl, triphenylmethyl, and the like; alkaryl radicals such as tolyl, xylyl, and the like; alicyclic radicals such as cyclopentyl, cyclohexyl, 1-methylcyclohexyl, cyclooctyl, cyclohexylethyl, and the like; alkoxy radicals such as methoxy, ethoxy, propoxy, t-butoxy-OCH$_2$CH$_2$OCH$_3$, —O(CH$_2$CH$_2$)$_2$OCH$_3$, —O(CH$_2$CH$_2$)$_3$OCH$_3$, and the like; aryloxy radicals such as phenoxy and the like; as well as silyl radicals such as —Si(CH$_3$)$_3$, —Si(OCH$_3$)$_3$, —Si(C$_3$H$_7$)$_3$, and the like; acyl radicals such as —C(O)CH$_3$, —C(O)C$_2$H$_5$, —C(O)C$_6$H$_5$, and the like; carbonyloxy radicals such as —C(O)OCH$_3$ and the like; oxycarbonyl radicals such as —O(CO)C$_6$H$_5$, and the like.

If desired, such monovalent substituents may in turn be substituted with any substituent which does not unduly adversely affect the purpose and process of this invention such as, for example, those hydrocarbon and non-hydrocarbon substituents outlined herein for $R^8$, $R^9$, $R^{10}$, $R^{11}$, $R^{12}$ and $R^{13}$. Formulas (IX) through (XI) are also intended to encompass compounds having two or more such diazole formulas, e.g., wherein two diazole formulas are directly bonded together as a result of any one of the $R^8$ to $R^{13}$ substituents optionally representing a direct bond or as a result of any one of the $R^8$ to $R^{13}$ substituents being optionally substituted with a second diazole formula.

Moreover, said adjacent substituents, $R^8$ and $R^{11}$, or $R^8$ and $R^9$, or $R^{10}$ and $R^{11}$, or $R^{10}$ and $R^{12}$, or $R^{12}$ and $R^{13}$, may be taken together to form a substituted or unsubstituted divalent bridging group having from 3 to 5, preferably 4, carbon atoms, which along with the two atoms shown in the formula to which they are bonded, form a 5 to 7 membered cyclic ring. Such divalent bridging groups preferably consist of only carbon atoms, but may contain from 1 to 2 nitrogen atoms in addition to said carbon atoms. Examples of substituents that may be on the substituted divalent bridging groups are the same hydrocarbon and non-hydrocarbon substituents as those defined herein for $R^8$, $R^9$, $R^{10}$, $R^{11}$, $R^{12}$ and $R^{13}$. Preferred diazoles are the imidazoles of Formula (IX) above, especially benzimidazoles.

Illustrative triazole compounds include the following:

(a) 1,2,3-triazoles represented by the formula:

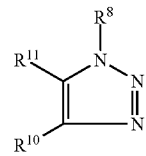

(XII)

(b) 1,2,4-triazoles represented by the formula:

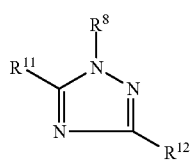

(XIII)

(c) 2,1,3-triazoles represented by the formula:

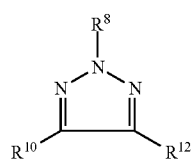

(XIV)

and (d) 4,1,2-triazoles represented by the formula:

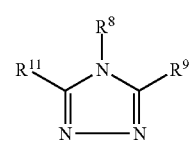

(XV)

wherein in Formulas (XII), (XIII), (XIV), and (XV) above, $R^8$, $R^9$, $R^{10}$, $R^{11}$ and $R^{12}$ are identical or different and each represents a hydrogen atom or a monovalent substituent, and adjacent substituents $R^8$ and $R^9$, or $R^8$ and $R^{11}$, or $R^{10}$ and $R^{11}$, or $R^{10}$, and $R^{12}$, may optionally be taken together to form a substituted or unsubstituted divalent radical which together with the two atoms of the formula to which said adjacent substituents are bonded form a cyclic ring. More specifically said monovalent substituents of $R^8$, $R^9$, $R^{10}$, $R^{11}$ and $R^{12}$ and the adjacent substituents $R^8$ and $R^9$, R[8] and R[11], R[10] and R[11], or R[10] and R[12], in Formulas (XII) to (XV) above, may be the same as the monovalent substituents and divalent radicals defined for Formulas (IX) to (XI) above. It is to be further understood that Formulas (XII) through (XV) are also intended to encompass compounds having two or more such triazole formulas, e.g., wherein two triazole formulas are directly bonded together as a result of any one of the R[8], R[9], R[10], R[11] and R[12] substituents optionally representing a direct bond or as a result of any one of the R[8], R[9], R[10], R[11] and R[12] substituents being optionally substituted with a second triazole formula. Preferred triazoles are the 1,2,3-triazoles of Formula (XII) above, especially benzotriazole. Other illustrative triazoles include 5-methyl-1H-benzotriazole, 5,6-dimethyl-1-H-benzotriazole, 1-hydroxybenzotriazole, 2-(2H-benzotriazole-2-yl)-4-(1,1,3,3-tetramethylbutyl)-phenol, 5-nitrobenzotriazole, bis(1-benzotriazolyl) oxalate, 1-benzotriazolyl 9-fluorenylmethyl carbonate, 1-cyanobenzotriazole, 2-(2H-benzotriazol-2-yl)-hydroquinone, 2-(2-hydroxy-5-methylphenyl)-benzotriazole, 5-hexylbenzotriazole, 5-decylbenzotriazole, 1-ethylbenzotriazole, 1-pentylbenzotriazole, 1-benzylbenzotriazole, 1-dodecylbenzotriazole, and the like.

Illustrative diazine compounds include the following:
(a) 1,2-diazines represented by the formula:

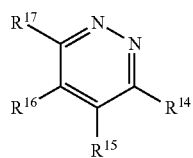

(XVI)

(b) 1,3-diazines represented by the formula:

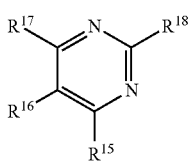

(XVII)

and (c) 1,4-diazines represented by the formula:

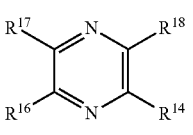

(XVIII)

wherein in Formulas (XVI), (XVII) and (XVIII) above, $R^{14}$, $R^{15}$, $R^{16}$, $R^{17}$ and $R^{18}$ are identical or different and each represents a hydrogen atom or a monovalent substituent, and adjacent substituents $R^{14}$ and $R^{15}$, or $R^{15}$ and $R^{16}$, or $R^{16}$ and $R^{17}$, or $R^{14}$ and $R^{18}$ may optionally be taken together to form a substituted or unsubstituted divalent radical which together with the two atoms of the formula to which said adjacent substituents are bonded form a cyclic ring. More specifically, said monovalent substituents $R^{14}$, $R^{15}$, $R^{16}$, $R^{17}$ and $R^{18}$, and the adjacent substituents $R^{14}$ and $R^{15}$, or $R^{15}$ and $R^{16}$, or $R^{16}$ and $R^{17}$, or $R^{14}$ and $R^{18}$, in Formulas (XVI) to (XVIII) above, may be the same as the monovalent substituents and divalent radicals defined for Formulas (IX) to (XI) above. It is to be further understood that Formulas (XVI) through (XVIII) are also intended to encompass compounds having two or more such diazine formulas, e.g., wherein two diazine formulas are directly bonded together as a result of any one of the $R^{14}$ to $R^{18}$ substituents optionally representing a direct bond or as a result of any one of the $R^{14}$ to $R^{18}$ substituents being optionally substituted with a second diazine formula. Illustrative of such diazine compounds are pyridazine, pyrimidine, pyrazine, and the like.

Illustrative triazine compounds include 1,3,5-triazines represented by the formula:

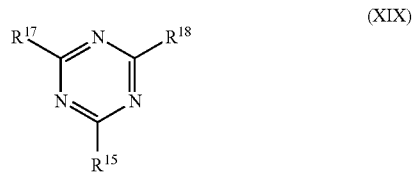

(XIX)

wherein in Formula (XIX) above, $R^{15}$, $R^{17}$, and $R^{18}$ are identical or different and each represents a hydrogen atom or a monovalent substituent. More specifically, said monovalent substituents $R^{15}$, $R^{17}$, and $R^{18}$ in Formula (XIX) above, may be the same as the monovalent substituents defined for Formulas (IX) to (XI) above. It is to be further understood that Formulas (XIX) is also intended to encompass compounds having two or more such triazine formulas, e.g., wherein two triazine formulas are directly bonded together as a result of any one of the $R^{15}$, $R^{17}$, and $R^{18}$ substituents optionally representing a direct bond or as a result of any one of the $R^{15}$, $R^{17}$, and $R^{18}$ substituents being optionally substituted with a second triazine formula. Illustrative of such triazines compounds are 1,3,5-triazine, and the like.

It is to be understood that the heterocyclic nitrogen stabilizing agents of the present invention contain at least one unfunctionalized nitrogen with a lone pair of electrons capable of forming a complex with the catalytic metal. In other words, ionic ammonium salts such as described in U.S. Pat. No. 6,995,293 B2 (either alkylated or protonated) are not heterocyclic nitrogen stabilizing agents, since these quaternary ammonium salts do not have a free nitrogen lone pair.

Any of the $R^8$ to $R^{18}$ radicals of such free heterocyclic nitrogen compounds of Formulas (IX) to (XIX) above may be substituted if desired, with any suitable substituent containing from 1 to 30 carbon atoms that does not unduly adversely affect the desired result of the process or this invention. Substituents that may be on said radicals in addition of course to corresponding hydrocarbon radicals such as alkyl, aryl, aralkyl, alkaryl and cyclohexyl substituents, may include for example amino radicals such as —N(R$^{19}$)$_2$; phosphine radicals such as -aryl-P(R$^{19}$)$_2$; acyl radicals such as —C(O)R$^{19}$ acyloxy radicals such as —OC(O)R$^{19}$; amido radicals such as —CON(R$^{19}$)$_2$ and —N(R$^{19}$)COR$^{19}$; sulfonyl radicals such as —SO$_2$R$^{19}$, alkoxy radicals such as —OR$^{19}$, sulfinyl radicals such as —SOR$^{19}$, sulfenyl radicals such as —SR$^{19}$, ionic radicals selected from the group consisting of: —SO$_3$M, —PO$_3$M, —N(R$^6$)$_3$X$^1$ and —CO$_2$M as defined herein above for ionic phosphines, wherein M, X$^1$ and R$^6$ are as defined above, as well as, nitro, cyano, trifluoromethyl, hydroxy radicals, and the like, wherein each R$^{19}$ radical individually represents the same or different monovalent hydrocarbon radical having from 1 to 18 carbon atoms (e.g., alkyl, aryl, aralkyl, alkaryl and cyclohexyl radicals), with the proviso that in amino substituents such as —N(R$^{19}$)$_2$ each R$^{19}$ taken together can also represent a divalent bridging group that forms a heterocyclic radical with the nitrogen atom. Of course it is to be understood that any of the substituted or unsubstituted substituent radicals that make up a particular given free heterocyclic nitrogen compound may be the same or different.

The more preferred free heterocyclic nitrogen compounds employable in this invention are the imidazoles of Formula (IX) above, especially benzimidazoles.

Illustrative specific examples include imidazole and substituted imidazoles, such as 1-methylimidazole, 1-ethylimidazole, 1-n-propylimidazole, 1-isopropylimidazole, 1-butylimidazole, 2-methylimidazole, 2-ethylimidazole, 2-n-propylimidazole, 2-isopropylimidazole, 2-n-butylimidazole, 2-n-hexylimidazole, 2-n-heptylimidazole, 2-n-octylimidazole, 2-n-nonylimidazole, 2-n-decyl-imidazole, 2-n-undecylimidazole, 2-n-dodecylimidazole, 2-n-tridecylimidazole, 2-n-tetradecylimidazole, 2-n-pentadecylimidazole, 2-n-hexadecylimidazole, 2-n-heptadecylimidazole, 2-(2-ethylpentyl)imidazole, 2-ethyl-4-methylimidazole, 2-phenylimidazole, 1-benzyl-2-methylimidazole, 2,4,5-triphenylimidazole, 2-(2-propylhexyl)imidazole, 4-methylimidazole, 4-ethylimidazole, 3-n-propylimidazole, 4-isopropylimidazole, 4-butylimidazole, 4,5-dimethylimidazole, 4,5-diethylimidazole, 1-methyl-2-ethylimidazole, 1-methyl-4-ethylimidazole, 2-ethyl-4-methylimidazole, 1-benzyl-2-methylimidazole, 1-phenylimidazole, 2-phenylimidazole, 4-phenylimidazole, 2,4,5-triphenylimidazole, 1,2-trimethyleneimidazole, 1,5-trimethyleneimidazole, 4,5-trimethyleneimidazole, and the like, as well as, polar substituted imidazoles, such as e.g., 1-hydroxymethylimidazole, 2-hydroxymethylimidazole, 4-hydroxymethylimidazole, 1-(2-hydroxyethyl) imidazole, 2(2-hydroxyethyl)imidazole, 4-2(hydroxyethyl)imidazole, 1-carboxymethylimidazole, 2-carboxymethylimidazole, 4-carboxymethylimidazole, 1(2-carboxyethyl)imidazole, 4-(2-carboxyethyl) imidazole, 4-(2-carboxyethyl)imidazole, 4-(2-carboxy-2-hydroxyethyl) imidazole, and the like.

The preferred benzimidazoles are those represented by the formula:

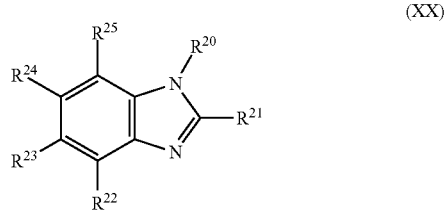

(XX)

wherein in Formula (XX) above $R^{20}$, $R^{21}$, $R^{22}$, $R^{23}$, $R^{24}$ and $R^{25}$ are identical or different and each represent a hydrogen atom or a monovalent substituent, provided $R^{20}$ and $R^{21}$ are not both a monovalent hydrocarbon radical at the same time. More specifically said monovalent substituents of $R^{20}$, $R^{21}$, $R^{22}$, $R^{23}$, $R^{24}$ and $R^{25}$ may be the same as those monovalent substituents defined for Formulas (IX) to (XI) above. Of course it is to be further understood that Formula (XX) is also intended to encompass compounds having two or more such benzimidazole formulas, e.g., wherein two benzimidazole formulas are directly bonded together as a result of any one of the $R^{20}$ to $R^{25}$ substituents, e.g., $R^{21}$, optionally representing a direct bond or as a result of any one of the $R^{20}$ to $R^{25}$ substituents, e.g., $R^{21}$, being optionally substituted with a second benzimidazole formula, e.g., di-, bi-, or bisbenzimidazoles.

Examples of such benzimidazoles include benzimidazole and substituted benzimidazoles, such as 1-methylbenzimidazole, 1-ethylbenzimidazole, 1-n-propylbenzimidazole, 1-isopropylbenzimidazole, 1-butylbenzimidazole, 1-benzylbenzimidazole, 2-benzylbenzimidazole, 2-methylbenzimidazole, 2-ethylbenzimidazole, 2-n-propylbenzimidazole, 2-isopropylbenzimidazole, 2-n-butylbenzimidazole, 2-n-hexylbenzimidazole, 2-n-heptylbenzimidazole, 2-n-octylbenzimidazole, 2-n-nonylbenzimidazole, 2-n-decylbenzimidazole, 2-n-undecylbenzimidazole, 2-n-dodecylbenzimidazole, 2-n-tridecylbenzimidazole, 2-n-tetradecylbenzimidazole, 2-n-pentadecylbenzimidazole, 2-n-hexadecylbenzimidazole, 2-n-heptadecylbenzimidazole, 2-(2-ethylpentyl)benzimidazole, 2-(2-propylhexyl)benzimidazole, 2-phenylbenzimidazole, 2-phenylbenzimidazole, 1-benzylimidazole, 1-, cyclohexylbenzimidazole, 1-octylbenzimidazole, 1-dodecylbenzimidazole, 1-hexyldecylbenzimidazole, 5,6-dimethylbenzimidazole, 1-methyl-5,6-dimethylbenzimidazole, 4-methylbenzimidazole, 4-ethylbenzimidazole, 3-n-propylbenzimidazole, 4-isopropylbenzimidazole, 4-butylbenzimidazole, 4,5-dimethylbenzimidazole, 4,5-diethylbenzimidazole, 1-methyl-2-ethylbenzimidazole, 1-methyl-4-ethylbenzimidazole, 1-phenylbenzimidazole, and 4-phenylbenzimidazole, 5-bromobenzotriazole, 6-bromobenzotriazole, 5-chlorobenzotriazole, 6-chlorobenzotriazole, 5-chloro-1,6-dimethylbenzotriazole 5-chloro-6-methylbenzotriazole, 6-chloro-5-methylbenzotriazole, 5-chloro-6-methyl-1-phenylbenzotriazole, 4,5,6,7-tetrachlorobenzotriazole, 1-(2-iodoethyl)benzotriazole, 5-chloro-6-fluorobenzotriazole, 5-trifluoromethylbenzotriazole, 6-trifluoromethylbenzotriazole, and the like, as well as, polar substituted benzimidazoles, such as 1-acetylbenzimidazole, 1-benzoylbenzimidazole, 1-hydroxymethylbenzimidazole, 2-hydroxymethylbenzimidazole, 4-hydroxymethylbenzimidazole, 1-(2-hydroxyethyl)benzimidazole, 2(2-hydroxyethyl)benzimidazole, 4-2(hydroxyethyl)benzimidazole, 1-carboxymethylbenzimidazole, 2-carboxymethylbenzimidazole, 4-carboxymethylbenzimidazole, 1(2-carboxyethyl) benzimidazole, 4-(2-carboxyethyl)benzimidazole, 4-(2-carboxyethyl)benzimidazole, 4-(2-carboxy-2-hydroxyethyl) benzimidazole, 1-ethyl-5,6-dimethylbenzimidazole, 1-isopropyl-5,6-benzimidazole, 1-isopropyl-5,6-benzimidazole, 5,6-dimethoxybenzirnidazole, 4,5-trimethylenebenzimidazole, naphtho[1,2-d]imidazole, naphtho[2,3-d]imidazole, 1-methyl-4-methoxybenzimidazole, 1-methyl-5-methoxybenzimidazole, 1-methyl-5,6-dimethoxybenzimidazole, and the like. Bi-, di- and bisbenzimidazoles are also included such as 2,2'-ethylenebibenzimidazole, 2,2'-heptamethylenebibenzimidazole, 2,2'-hexamethylenebibenzimidazole, 2,2'(iminodiethylidene)-bibenzimidazole, 2,2'-(methyliminodiethylidene) bibenzimidazole, 2,2'-octamethylenebibenzimidazole, 2,2'pentamethylenebibenzimidazole, 2,2-p-phenylenebibenzimidazole, 2,2'-trimethylenebibenzimidazole, 2,2'-methylene bis(5,6-dimethylbenzimidazole), di-2-benzimidazolylmethane, 5,5',6,6'-tetramethyl-2,2'-bibenzimidazole and 1,2-bis(5,6-dimethyl-2-benzimidazolyl)ethanol hydrochloride, and the like. The most preferred heterocyclic nitrogen compound of all is benzimidazole.

Benzimidazoles and benzotriazoles are preferred heterocyclic nitrogen stabilizing agents. Moreover the amount of such free heterocyclic nitrogen compounds employable in any given process of this invention need only be that minimum amount necessary to furnish the basis for at least some minimization of catalyst deactivation as might be found to occur as a result of carrying out an identical metal catalyzed hydroformylation process under essentially the same conditions, but in the absence of any free heterocyclic nitrogen compound during harsh conditions, such as vaporization separation of the aldehyde product. The amount of heterocyclic nitrogen stabilizing agent advantageously ranges from 0.001 up to 10 weight percent, or higher if desired, based on the total weight of the hydroformylation reaction product fluid in the reactor. In one embodiment of the invention, the amount of heterocyclic nitrogen stabilizing agent is from 0.05 to about 5 weight percent. As the aldehyde product is separated from the hydroformylation product fluid, the concentration of the non-volatilized components therein, e.g., the catalyst and free heterocyclic nitrogen compound, will increase accordingly. Thus the upper amount of free heterocyclic nitrogen compound is governed primarily by its solubility limit in the non-volatilized liquid rhodium catalyst containing residue obtained after such vaporization separation of the aldehyde product, e.g., distillation removal of as much of the aldehyde product desired. The amount of the heterocyclic nitrogen stabilizing agent employed will also depend in part upon the particular rhodium catalyst employed and the vaporization separation temperature for recovering the aldehyde product, as well as the particular the heterocyclic nitrogen stabilizing agent itself.

The addition of the heterocyclic nitrogen stabilizing agent to the reaction product fluid from which the aldehyde product is to be distilled may be carried out in any suitable manner desired. For instance, the heterocyclic nitrogen stabilizing agent may be added to the hydroformylation reaction product fluid that has been removed from the reaction zone and at any time prior to or during the distillation of the aldehyde product therefrom. However, since the heterocyclic nitrogen stabilizing agent chosen to be used should not have any substantial detrimental effect on the hydroformylation reaction per se, the free heterocyclic nitrogen compound may be added directly to the hydroformylation reaction medium in the reaction zone and allowed to remain in solution throughout the entire hydroformylation process. Indeed, it may be desirable to add the free heterocyclic nitrogen compound to the precursor catalyst solution to be employed so that the free heterocyclic nitrogen compound is present right from the start of the hydroformylation process.

The hydroformylation process, and conditions for its operation, are well known. The hydroformylation process may be asymmetric or non-asymmetric, the preferred process being non-asymmetric, and may be conducted in any batch, continuous or semi-continuous fashion and may involve any catalyst liquid and/or gas recycle operation desired.

The particular hydroformylation process for producing such aldehydes from an olefinic unsaturated compound, as well as the reaction conditions and ingredients of the hydroformylation process are not critical features of this invention. The process of this invention adopts the variables of the invention of U.S. Pat. No. 3,527,809, and by experiences from operations herein described establishes the tremendous advance that invention represents in the Oxo art.

The recycle procedure generally involves withdrawing a portion of the liquid reaction medium containing the catalyst and aldehyde product from the hydroformylation reactor, i.e., reaction zone, either continuously or intermittently, and recovering the aldehyde product therefrom by use of a composite membrane, such as disclosed in U.S. Pat. No. 5,430,194 and U.S. Pat. No. 5,681,473, or by the more conventional and preferred method of distilling it, i.e., vaporization separation, in one or more stages under normal, reduced or elevated pressure, as appropriate, in a separate distillation zone, the non-volatilized metal catalyst containing residue being recycled to the reaction zone as disclosed, for example, in U.S. Pat. No. 5,288,918. Condensation of the volatilized materials, and separation and further recovery thereof, e.g., by further distillation, can be carried out in any conventional manner, the crude aldehyde product can be passed on for further purification and isomer separation, if desired, and any recovered reactants, e.g., olefinic starting material and syngas, can be recycled in any desired manner to the hydroformylation zone (reactor). The recovered metal catalyst containing raffinate of such membrane separation or recovered non-volatilized metal catalyst containing residue of such vaporization separation can be recycled, to the hydroformylation zone (reactor) in any conventional manner desired.

In a preferred embodiment, the hydroformylation reaction fluid includes any fluid derived from any corresponding hydroformylation process that contains at least some amount of four different main ingredients or components, i.e., the aldehyde product, a metal-organophosphorus ligand complex catalyst, free organophosphorus ligand and a solvent for said catalyst and said free ligand. The hydroformylation reaction mixture compositions can and normally will contain additional ingredients such as those that have either been deliberately employed in the hydroformylation process or formed in situ during said process. Examples of such additional ingredients include unreacted olefin starting material, carbon monoxide and hydrogen gases, and in situ formed by-products, such as saturated hydrocarbons and/or unreacted isomerized olefins corresponding to the olefin starting materials, ligand degradation compounds, and high boiling liquid aldehyde condensation by-products, as well as other inert co-solvent type materials or hydrocarbon additives, if employed. In one embodiment, the reaction fluid is substantially free of chloride ions and chloride compounds.

The reaction conditions of the hydroformylation processes may include any suitable type hydroformylation conditions heretofore employed for producing optically active and/or non-optically active aldehydes. The hydroformylation reaction conditions employed will be governed by the type of aldehyde product desired. For instance, the total gas pressure of hydrogen, carbon monoxide and olefin starting compound of the hydroformylation process may range from 1 to 69,000 kPa. In general, however, it is preferred that the process be operated at a total gas pressure of hydrogen, carbon monoxide and olefin starting compound of less than 14,000 kPa and more preferably less than 3,400 kPa. The minimum total pressure is limited predominately by the amount of reactants necessary to obtain a desired rate of reaction. More specifically, the carbon monoxide partial pressure of the hydroformylation process is preferably from 1 to 6,900 kPa, and more preferably from 21 to 5,500 kPa, while the hydrogen partial pressure is preferably from 34 to 3,400 kPa and more preferably from 69 to 2,100 kPa. In general, the molar ratio of gaseous $H_2:CO$ may range from 1:10 to 100:1 or higher, the more preferred molar ratio being from 1:10 to 10:1.

In general, the hydroformylation process may be conducted at any operable reaction temperature. Advantageously, the hydroformylation process is conducted at a reaction temperature from $-25°$ C. to $200°$ C., preferably from $50°$ C. to $120°$ C.

The hydroformylation processes may be carried out using one or more suitable reactors such as, for example, a fixed bed reactor, a fluid bed reactor, a continuous stirred tank reactor (CSTR) or a slurry reactor. The optimum size and shape of the catalysts will depend on the type of reactor used. The reaction zone employed may be a single vessel or may comprise two or more discrete vessels. The separation zone employed may be a single vessel or may comprise two or more discrete vessels. The buffer treatment zone employed in this invention may be a single vessel or may comprise two or more discreet vessels. The reaction zone(s) and separation zone(s) employed herein may exist in the same vessel or in different vessels. For example, reactive separation techniques such as reactive distillation, and reactive membrane separation may occur in the reaction zone(s).

The hydroformylation processes can be conducted with recycle of unconsumed starting materials if desired. The reaction can be conducted in a single reaction zone or in a plurality of reaction zones, and in series or in parallel. The reaction steps may be affected by the incremental addition of one of the starting materials to the other. Also, the reaction steps can be combined by the joint addition of the starting materials. When complete conversion is not desired or not obtainable, the starting materials can be separated from the product, for example by distillation, and the starting materials then recycled back into the reaction zone.

The hydroformylation processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

The hydroformylation processes of this invention may be conducted in one or more steps or stages. The exact number of reaction steps or stages will be governed by the best compromise between capital costs and achieving high catalyst selectivity, activity, lifetime and ease of operability, as well as the intrinsic reactivity of the starting materials in question and the stability of the starting materials and the desired reaction product to the reaction conditions.

In one embodiment, the hydroformylation processes useful in this invention may be carried out in a multistaged reactor such as described, for example, in U.S. Pat. No. 5,728,893. Such multistaged reactors can be designed with internal, physical barriers that create more than one theoretical reactive stage per vessel.

It is generally preferred to carry out the hydroformylation processes in a continuous manner. Continuous hydroformylation processes are well known in the art. The continuous process can be carried out in a single pass mode, i.e., wherein a vaporous mixture comprising unreacted olefinic starting material(s) and vaporized aldehyde product is removed from the liquid reaction mixture from whence the aldehyde product is recovered and make-up olefinic starting material(s), carbon monoxide and hydrogen are supplied to the liquid reaction medium for the next single pass through without recycling the unreacted olefinic starting material(s). Such types of recycle procedure are well known in the art and may involve the liquid recycling of the metal-organophosphorus complex catalyst fluid separated from the desired aldehyde reaction product(s), such as disclosed, for example, in U.S. Pat. No. 4,148,830 or a gas recycle procedure such as disclosed, for example, in U.S. Pat. No. 4,247,486, as well as a combination of both a liquid and gas recycle procedure if desired. The most preferred hydroformylation process comprises a continuous liquid catalyst recycle process. Suitable liquid catalyst recycle procedures are disclosed, for example, in U.S. Pat. Nos. 4,668,651; 4,774,361; 5,102,505 and 5,110,990.

In one embodiment, the aldehyde product mixtures may be separated from the other components of the crude reaction mixtures in which the aldehyde mixtures are produced by any suitable method such as, for example, solvent extraction, crystallization, distillation, vaporization, wiped film evaporation, falling film evaporation, phase separation, filtration, or any combination thereof. It may be desired to remove the aldehyde products from the crude reaction mixture as they are formed through the use of trapping agents as described in WO 88/08835. One method for separating the aldehyde mixtures from the other components of the crude reaction mixtures is by membrane separation, which is described, for example in U.S. Pat. Nos. 5,430,194 and 5,681,473.

As indicated above, desired aldehydes may be recovered from the reaction mixtures. For example, the recovery techniques disclosed in U.S. Pat. Nos. 4,148,830 and 4,247,486 can be used. For instance, in a continuous liquid catalyst recycle process the portion of the liquid reaction mixture (containing aldehyde product, catalyst, etc.), i.e., reaction fluid, removed from the reaction zone can be passed to a separation zone, e.g., vaporizer/separator, wherein the desired aldehyde product can be separated via distillation, in one or more stages, under normal, reduced or elevated pressure, from the liquid reaction fluid, condensed and collected in a product receiver, and further purified if desired. The remaining non-volatilized catalyst containing liquid reaction mixture may then be recycled back to the reactor as may if desired any other volatile materials, e.g., unreacted olefin, together with any hydrogen and carbon monoxide dissolved in the liquid reaction after separation thereof from the condensed aldehyde product, e.g., by distillation in any conventional manner. In general, it is preferred to separate the desired aldehydes from the catalyst-containing reaction mixture under reduced pressure and at low temperatures so as to avoid possible degradation of the organophosphorus ligand and reaction products.

More particularly, distillation and separation of the desired aldehyde product from the metal-organophosphorus complex catalyst containing reaction fluid may take place at any suitable temperature desired. In general, it is preferred that such distillation take place at relatively low temperatures, such as below 150° C., and more preferably at a temperature in the range of from 50° C. to 140° C. It is also generally preferred that such aldehyde distillation take place under reduced pressure, e.g., a total gas pressure that is substantially lower than the total gas pressure employed during hydroformylation when low boiling aldehydes (e.g., $C_4$ to $C_6$) are involved or under vacuum when high boiling aldehydes (e.g., $C_7$ or greater) are involved. For instance, a common practice is to subject the liquid reaction product medium removed from the hydroformylation reactor to a pressure reduction so as to volatilize a substantial portion of the unreacted gases dissolved in the liquid medium that now contains a much lower synthesis gas concentration than is present in the reaction medium to the distillation zone, e.g., vaporizer/separator, wherein the desired aldehyde product is distilled. In general, distillation pressures ranging from vacuum pressures on up to total gas pressure of 340 kPa should be sufficient for most purposes.

Illustrative non-optically active aldehyde products include e.g., propionaldehyde, n-butyraldehyde, isobutyraldehyde, n-valeraldehyde, 2-methyl 1-butyraldehyde, hexanal, hydroxyhexanal, 2-methyl 1-heptanal, nonanal, 2-methyl-1-octanal, decanal, adipaldehyde, 2-methylglutaraldehyde, 2-methyladipaldehyde, 3-hydroxypropionaldehyde, 6-hydroxyhexanal, alkenals, e.g., 2-, 3- and 4-pentenal, alkyl 5-formylvalerate, 2-methyl-1-nonanal, 2-methyl 1-decanal, 3-propyl-1-undecanal, pentadecanal, 3-propyl-1-hexadecanal, eicosanal, 2-methyl-1-tricosanal, pentacosanal, 2-methyl-1-tetracosanal, nonacosanal, 2-methyl-1-octacosanal, hentriacontanal, 2-methyl-1-triacontanal, and the like.

Illustrative optically active aldehyde products include (enantiomeric) aldehyde compounds prepared by the asymmetric hydroformylation process of this invention such as, e.g., S-2-(p-isobutylphenyl)-propionaldehyde, S-2-(6-methoxy-2-naphthyl)propionaldehyde, S-2-(3-benzoylphenyl)-propionaldehyde, S-2-(2-methylacetaldehyde)-5-benzoylthiophene and the like.

SPECIFIC EMBODIMENTS OF THE INVENTION

All parts and percentages in the following examples are by weight unless otherwise indicated. Pressures are given as absolute pressure unless otherwise indicated.

As described below, an accelerated testing procedure has been devised for demonstrating the potential effectiveness of free heterocyclic nitrogen compounds for minimizing or preventing such catalytic aleactivation and/or rhodium loss as discussed herein that may occur during a continuous liquid recycle hydroformylation involving the use of a rhodium-triarylphosphine ligand complex catalyst and vaporization separation i.e., distillative recovery of the desired aldehyde product. Said testing procedure is outlined in certain of the following examples and comprises subjecting a solubilized activated rhodium-triarylphosphine ligand complex catalyst containing reaction product fluid to harsh vaporizer type conditions for a much longer sustained period of time than would be experienced during a normal continuous liquid recycle hydroformylation process in order to obtain meaningful results in a much shorter and manageable period of time. For instance, the catalytic deactivation and/or rhodium loss as discussed herein that may occur during a continuous liquid recycle hydroformylation such may take days or weeks to define quantitatively under normal aldehyde distillative recovery procedures because the catalyst is subjected to such vaporizer conditions for only a matter of a few minutes each day, whereas the accelerated test can be completed within hours by continuously maintaining the reaction product fluid at high aldehyde recovery type distillation temperatures for a prolonged period of time in the total absence of carbon monoxide.

The effect of benzimidazole (BZIM) on rhodium catalyzed aryl exchange is examined under conditions that would accelerate ligand decomposition and rhodium clustering. Triphenylphosphine (TPP) and tri-(p-toyly)phosphine are chosen because they are known to undergo scrambling (see Scheme 1) and the resultant products can be quantified by gas chromatography (GC). All of the experiments for the data shown in Tables 1-6 are run in tetraglyme solvent at 150° C., 1500 ppm Rh (from RhAcetylacetonate $(CO)_2$), 2 wt. % each of triphenylphosphine and tri-(p-tolyl) phosphine, and an initial total pressure of approximately 100 psig (689 kPa·g) of the various gases studied. Trioctylphosphine oxide (TOPO) is added to the runs as an internal standard, and the samples taken with time are oxidized with tert-butylhydroperoxide to avoid subsequent reaction during analysis by GC. Thus, TPP is converted to TPPO and reported as such (other phosphines would likewise be converted to their corresponding oxides). In experiments where secondary scrambling products are observed ($Pr_2PPh$, $Pr_2P$ (p-Tol) and $Pr_3P$ for example) the amounts are small and are not included in the analysis.

Scheme 1.
Rhodium catalyzed scrambling of aryl groups between TPP and tri-(paratolyl)phosphine ((p-Tol)$_3$P) results in formation of diphenylparatolylphosphine (Ph$_2$(p-Tol)P) and phenyl-di-paratolylphosphine (Ph(p-Tol)$_2$P).

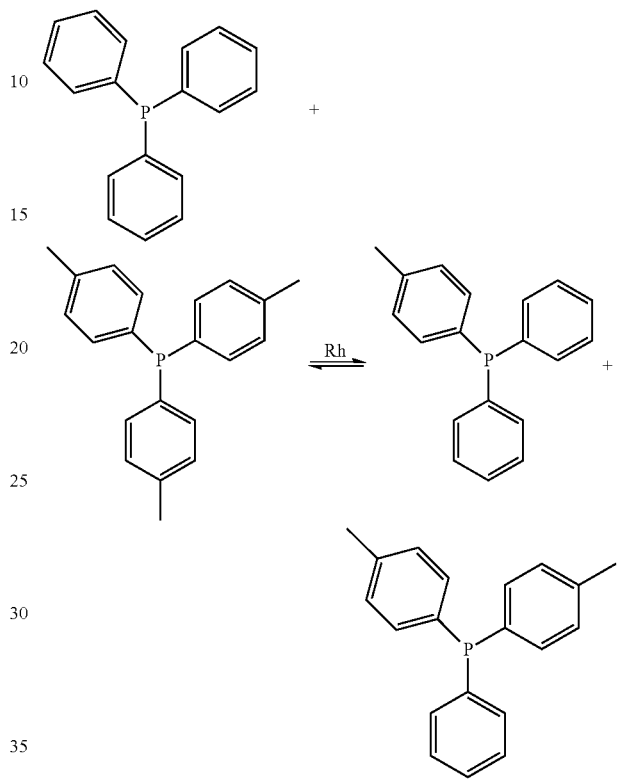

Comparative Experiment A (Propylene Only)—not an Embodiment of the Invention

The reactions are run under propylene alone and the results are given in Table 1. In the absence of BZIM, the exchange of phenyl with p-tolyl groups at phosphorus occurs at a rate such that approximately a third of each starting ligand is converted over the course of the three hour study. Under these conditions, no hydrogen is present for the formation of propyl substituted phosphines.

TABLE 1

Comparitive Experiment under Propylene only but without BZIM-demonstrating rapid aryl exchange between tri-arylphosphines.

Normalized Percent Composition of Phosphorous Ligands by $^{31}$P NMR

| TIME MIN | TPPO | % decline | Ph2(p-Tol)PO | Ph(p-Tol)2PO | (p-Tol)3PO | % decline | IntStd. TOPO |
|---|---|---|---|---|---|---|---|
| 0 | 38.5 |  | 0.2 | 0.6 | 45.2 |  | 15.5 |
| 0 | 39.2 |  | 0.2 | 0.7 | 44.2 |  | 15.7 |
| 15 | 38.3 | 1% | 0.8 | 1.2 | 43.8 | 2% | 15.8 |
| 30 | 37.1 | 4% | 2.0 | 2.5 | 42.7 | 5% | 15.8 |
| 60 | 35.2 | 9% | 4.3 | 4.9 | 39.9 | 11% | 15.7 |
| 75 | 34.3 | 12% | 5.1 | 5.7 | 39.1 | 12% | 15.7 |
| 90 | 31.1 | 20% | 8.5 | 9.3 | 35.2 | 21% | 16.0 |
| 120 | 29.2 | 25% | 10.6 | 11.5 | 32.4 | 28% | 16.2 |
| 150 | 27.4 | 29% | 12.4 | 13.4 | 30.5 | 32% | 16.2 |
| 180 | 26.4 | 32% | 13.5 | 14.5 | 29.1 | 35% | 16.5 |

Example 1

The procedure of Comparative Experiment A is repeated, except that 1 wt. % BZIM is added at the beginning. The results are shown in Table 2, and show essentially no aryl interchange over the same time period.

TABLE 2

Example with BZIM (under propylene) demonstrating essentially no aryl exchange between tri-arylphosphines.

| TIME | Normalized Percent Composition of Phosphorus Ligands by $^{31}$P NMR | | | | | | IntSd. |
|---|---|---|---|---|---|---|---|
| MIN | TPPO | % Decline | Ph2(p-Tol)PO | Ph(p-Tol)2PO | (p-Tol)3PO | % Decline | TOPO |
| 0 | 42.97 | | 0.06 | 0.31 | 41.61 | | 15.05 |
| 0 | 42.55 | | 0.11 | 0.55 | 41.98 | | 14.81 |
| 21 | 42.93 | 0% | 0.14 | 0.53 | 41.58 | 1% | 14.83 |
| 38 | 42.66 | 0% | 0.16 | 0.55 | 42.02 | −1% | 14.60 |
| 55 | 42.66 | 0% | 0.15 | 0.51 | 42.05 | −1% | 14.63 |
| 87 | 42.48 | 1% | 0.14 | 0.50 | 42.32 | −1% | 14.57 |
| 128 | 42.72 | 0% | 0.18 | 0.56 | 41.93 | 0% | 14.62 |
| 150 | 42.40 | 1% | 0.21 | 0.88 | 42.18 | −1% | 14.33 |
| 180 | 42.82 | 0% | 0.23 | 0.80 | 41.57 | 1% | 14.58 |
| 220 | 42.56 | 0% | 0.24 | 1.04 | 41.86 | 0% | 14.30 |
| 240 | 43.23 | −1% | 0.32 | 0.94 | 40.99 | 2% | 14.52 |
| 280 | 42.35 | 1% | 0.22 | 0.97 | 42.31 | −1% | 14.14 |

Comparative Experiment B (Hydrogen Only)—not an Embodiment of the Invention

The reaction is performed under hydrogen alone and the results are given in Table 3. The scrambling reaction is much faster than under propylene alone and clearly 50% of the initial ligands are consumed after roughly 2 hours.

TABLE 3

Comparitive Example under Hydrogen only and without BZIM demonstrating rapid aryl exchange between tri-arylphosphines.

| | Normalized Percent Composition of Phosphorous Ligands by $^{31}$P NMR | | | | | | |
|---|---|---|---|---|---|---|---|
| TIME MIN | TPPO | % Decline | Ph2(p-Tol)PO | Ph(p-Tol)2PO | (p-Tol)3PO | % Decline | IntStd. TOPO |
| 0 | 42.4 | | 0.2 | 0.6 | 41.7 | | 15.2 |
| 0 | 36.9 | | 1.6 | 2.0 | 43.5 | | 16.0 |
| 25 | 25.8 | 35% | 14.0 | 14.1 | 28.9 | 32% | 17.1 |
| 35 | 24.2 | 39% | 15.7 | 15.9 | 27.0 | 37% | 17.2 |
| 65 | 21.7 | 45% | 18.4 | 18.6 | 23.7 | 44% | 17.6 |
| 95 | 20.1 | 49% | 20.0 | 20.2 | 21.8 | 49% | 17.9 |
| 125 | 19.5 | 51% | 20.6 | 20.7 | 21.0 | 51% | 18.1 |
| 160 | 18.4 | 54% | 21.4 | 21.8 | 20.4 | 52% | 18.0 |
| 190 | 18.3 | 54% | 21.7 | 22.0 | 20.0 | 53% | 18.1 |

Example 2

Comparative Experiment B is repeated, except that 1 wt. % BZIM is added at the beginning. The results are shown in Table 4, and show substantially less aryl interchange over the same time period. Furthermore, in the presence of BZIM, the composition appears to be leveling off well before reaching the apparent equilibrium mixture seen in the Comparative Experiment B (i.e., in the absence of BZIM).

TABLE 4

Example with BZIM (under hydrogen) demonstrating substantially reduced aryl exchange between tri-arylphosphines compared to without BZIM.

| TIME | Normalized Percent Composition of Phosphorus Ligands by $^{31}$P NMR | | | | | | IntStd |
|---|---|---|---|---|---|---|---|
| MIN | TPPO | % decline | Ph2(p-Tol)PO | Ph(p-Tol)2PO | (p-Tol)3PO | % decline | TOPO |
| 0 | 40.2 | | 0.1 | 0.5 | 43.4 | | 15.9 |
| 0 | 39.4 | | 0.4 | 0.8 | 43.2 | | 16.2 |
| 15 | 35.9 | 10% | 3.7 | 4.1 | 39.5 | 9% | 16.9 |
| 25 | 34.0 | 15% | 5.6 | 6.1 | 37.4 | 14% | 16.9 |
| 60 | 32.0 | 20% | 7.7 | 8.2 | 35.1 | 19% | 17.0 |
| 95 | 30.8 | 22% | 8.9 | 9.5 | 33.6 | 23% | 17.2 |

TABLE 4-continued

Example with BZIM (under hydrogen) demonstrating substantially reduced aryl exchange between tri-arylphosphines compared to without BZIM.

| TIME | Normalized Percent Composition of Phosphorus Ligands by $^{31}$P NMR | | | | | IntStd |
|---|---|---|---|---|---|---|
| MIN | TPPO | % decline | Ph2(p-Tol)PO | Ph(p-Tol)2PO | (p-Tol)3PO | % decline | TOPO |
| 125 | 30.4 | 24% | 9.4 | 10.0 | 32.9 | 24% | 17.3 |
| 160 | 30.1 | 24% | 9.7 | 10.3 | 32.7 | 24% | 17.2 |
| 190 | 30.0 | 24% | 9.8 | 10.5 | 32.3 | 25% | 17.4 |

Comparative Experiment C—not an Embodiment of the Invention

Comparative Experiment A is repeated, except under a 1:1 propylene:hydrogen gas mixture. This shows the fastest rates of overall ligand scrambling so far and introduces another ligand degradation pathway, shown below in Scheme 2, which introduces propyl moieties onto the phosphorus (see Table 5 where "Pr$_x$Ph$_y$PO" represents the new propyl-substituted phosphine oxides). Nearly all of the starting TPP and (p-Tol)$_3$P has been consumed.

Without wishing to be bound by any theory, this is most likely related to the ability of this gas mixture to essentially react CO off of the Rh centers and make vacant binding sites for formation of Rh aggregates and ligand scrambling reactions. In the absence of BZIM, the aryl exchanged phosphines Ph$_2$(p-Tol)P and Ph(p-Tol)$_2$P have reached their maximum concentration within the 20 minute interval to the first sample. Subsequent exchange of propyl substituents into the mixture of aryl phosphines then occurs more slowly, but steadily, over the remainder of the run.

Scheme 2.
In the presence of propylene and hydrogen, the rhodium catalyzed ligand scrambing reactions result in additional propyl substituted ligands.
Propyldiphenylphosphine (Pr(Ph)$_2$P), Propyldi-(paratolyl)phosphine (Pr(p-Tol)$_2$P), and Propyl(phenyl)(paratolyl)phosphine (Pr(Ph)(p-Tol)P) are shown. Lesser amounts of further exchanges phosphines are also formed.

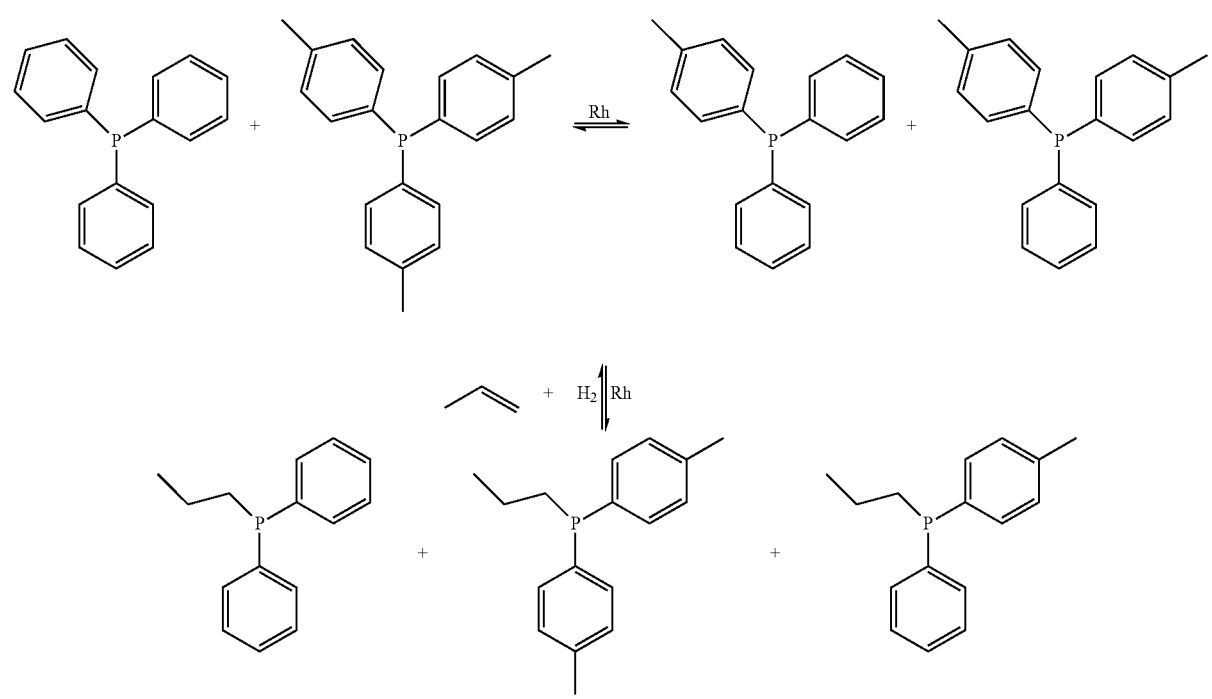

TABLE 5

Comparitive Example under 1:1 H$_2$:Propylene but without BZIM demonstrating rapid aryl exchange between tri-arylphosphines and propyl group insertion.

| | Normalized Percent Composition of Phosphorus Ligands by $^{31}$P NMR | | | | | | | |
|---|---|---|---|---|---|---|---|---|
| TIME MIN | TPPO | % Decline | Ph2(p-Tol)PO | "Pr$_x$Ph$_y$PO" | Ph(p-Tol)2PO | (p-Tol)3PO | % Decline | IntStd. TOPO |
| 0 | 38.8 | | 0.2 | 0.0 | 0.5 | 44.5 | | 16.0 |
| 0 | 32.8 | | 6.6 | 0.1 | 7.3 | 36.8 | | 16.3 |
| 15 | 12.9 | 64% | 23.4 | 8.5 | 23.6 | 15.0 | 63% | 16.6 |

TABLE 5-continued

Comparitive Example under 1:1 H$_2$:Propylene but without BZIM demonstrating rapid aryl exchange between tri-arylphosphines and propyl group insertion.

Normalized Percent Composition of Phosphorus Ligands by $^{31}$P NMR

| TIME MIN | TPPO | % Decline | Ph2(p-Tol)PO | "Pr$_x$Ph$_y$PO" | Ph(p-Tol)2PO | (p-Tol)3PO | % Decline | IntStd. TOPO |
|---|---|---|---|---|---|---|---|---|
| 30 | 9.7 | 73% | 23.3 | 13.7 | 24.2 | 11.7 | 71% | 17.3 |
| 60 | 7.6 | 79% | 20.8 | 21.1 | 22.7 | 10.0 | 75% | 17.8 |
| 110 | 6.6 | 82% | 18.2 | 27.4 | 20.4 | 9.1 | 78% | 18.4 |
| 170 | 6.1 | 83% | 16.8 | 30.6 | 19.1 | 8.7 | 79% | 18.6 |
| 210 | 5.9 | 84% | 16.0 | 32.5 | 18.3 | 8.4 | 79% | 18.9 |

Example 3

Comparative Experiment C is repeated, except that 1 wt. % BZIM is added at the beginning. The results are shown in Table 6.

TABLE 6

Example with BZIM (under 1:1 H$_2$:propylene) demonstrating substantially reduced aryl exchange between tri-arylphosphines and propylene insertion (compared to without BZIM in Table 5).

Normalized Percent Composition of Phosphorus Ligands by $^{31}$P NMR

| TIME MIN | TPPO | % decline | Ph2(p-Tol)PO | "Pr$_x$Ph$_y$PO" | Ph(p-Tol)2PO | (p-Tol)3PO | % decline | IntStd TOPO |
|---|---|---|---|---|---|---|---|---|
| 0 | 40.4 | | 0.0 | 0.0 | 0.0 | 43.6 | | 15.9 |
| 0 | 39.2 | | 1.2 | 0.0 | 1.6 | 42.0 | | 16.0 |
| 15 | 31.1 | 22% | 9.2 | 1.3 | 8.9 | 33.4 | 22% | 16.0 |
| 30 | 26.5 | 33% | 13.4 | 2.2 | 12.8 | 28.9 | 32% | 16.2 |
| 60 | 19.3 | 52% | 20.0 | 4.3 | 19.1 | 21.1 | 51% | 16.2 |
| 120 | 12.6 | 68% | 24.8 | 7.9 | 24.4 | 13.8 | 68% | 16.4 |
| 180 | 10.6 | 73% | 25.4 | 10.3 | 25.4 | 11.7 | 73% | 16.6 |
| 240 | 9.6 | 76% | 25.1 | 12.4 | 25.5 | 10.7 | 75% | 16.6 |

Based on comparison of the rate of loss of Ph$_3$P and (p-Tol)$_3$P, having BZIM present under 1:1 propylene/hydrogen reduces the rate of scrambling of aryl and propyl substituents into triaryl phosphine ligands by approximately a factor of ten.

Example 4

Catalyst Deactivation Under 1:1 Hydrogen/Carbon Monoxide

To demonstrate the effects of BZIM as an additive with TPP/Rh catalysts under 1:1 H$_2$/CO, two catalyst solutions are prepared with 1500 ppm Rh and 2 wt. % TPP in tetraglyme, and 1 wt. % BZIM is added to one of the catalyst solutions. The catalysts solutions are charged to separate Fisher-Porter™ bottles under inert conditions and heated under 60 psig (414 kPa·g) H$_2$:CO (1:1) at 110° C. for 2.5 hrs. After heating, 1 milliliter of catalyst is pulled from each bottle and diluted with ~13 grams tetraglyme. From the diluted catalyst solutions, ~10 milliliters are charged to a mini-reactor and placed under 90 psi (621 kPa·g) of H$_2$:CO:Propylene (1:1:1) at 90° C. The times required to consume 5 psi (34 kPa) of gas are recorded until constant and are shown in Table 1.

The catalyst samples are subjected to conditions favoring rhodium cluster formation. Following this treatment, the catalyst sample to which BZIM is added is approximately fifty percent more active than the sample without BZIM added. The run without BZIM added has approximately 67% of the activity of the run with BZIM.

TABLE 7

Times required for 5 psi pressure drops in mini-reactor evaluation of catalyst activity following accelerated deactivation under 1:1, CO/H$_2$.

| Reading Number | Time (Seconds) |
|---|---|
| BZIM Added: | |
| 1 | 124 |
| 2 | 233 |
| 3 | 208 |
| 4 | 218 |
| 5 | 210 |
| 6 | 212 |
| 7 | 220 |
| 8 | 218 |
| No BZ1M Added (not of the invention) | |
| 1 | 150 |
| 2 | 222 |
| 3 | 330 |
| 4 | 292 |
| 5 | 310 |
| 6 | 316 |
| 7 | 313 |
| 8 | 318 |

Example 5

Catalyst Deactivation Under 1:1 Hydrogen/Propylene

To demonstrate the effects of BZIM as an additive with TPP/Rh catalysts under 1:1 hydrogen/propylene, two catalyst solutions are prepared with 1500 ppm Rh and 2 wt. % TPP in tetraglyme. Benzimidazole (1 wt. %) is added to one of the catalyst solutions. The catalyst solutions are charged to separate Fisher-Porter™ bottles under inert conditions and heated under 80 psi (551 kPa) of 1:1 propylene/hydrogen at 110° C. for 15 hrs. After heating, 15 milliliters of the catalyst are syringed out and tested in a minireactor under 90 psi (621 kPa) of $H_2$/CO/Propylene (1:1:1) at 90° C. The times required to consume 5 psi (34 kPa) of gas are recorded and are shown in Table 8. These tests subject catalyst samples to conditions that accelerate propyldiphenylphosphine formation and rhodium clustering.

TABLE 8

Times required for 5 psi pressure drops in mini-reactor evaluation of catalyst activity following accelerated deactivation under 1:1, propylene/hydrogen.

| Reading Number | Time (Seconds) |
|---|---|
| BZ1M Added | |
| 1 | 18 |
| 2 | 25 |
| 3 | 27 |
| 4 | 28 |
| 5 | 28 |
| 6 | 30 |
| 7 | 35 |
| 8 | 36 |
| 9 | 36 |
| 10 | 37 |
| No BZIM Added (not of the invention) | |
| 1 | 45 |
| 2 | 189 |
| 3 | 740 |
| 4 | — |

The sample with BZIM added retained activity, while that without BZIM is essentially inactive.

What is claimed is:

1. A hydroformylation process comprising:
contacting in a reaction zone reactants comprising an olefin, hydrogen and CO in the presence of a metal-triorganophosphine ligand complex catalyst, wherein the metal of the catalyst comprises at least one of rhodium and cobalt, and, optionally, free triorganophosphine ligand, under hydroformylation reaction conditions sufficient to produce an aldehyde product in a reaction fluid, with the proviso that the contacting is conducted in the presence of from 0.001 to 10 weight parts of a heterocyclic nitrogen stabilizing agent based on 100 weight parts of catalyst solution in the reaction zone.

2. The process of claim 1 wherein the triorganophosphine ligand in the metal-triorganophosphine ligand complex catalyst comprises a triarylphosphine.

3. The process of claim 1 wherein the triorganophosphine ligand in the metal-triorganophosphine ligand complex catalyst comprises triphenylphosphine.

4. The process of claim 1 wherein the process is a continuous process.

5. The process of claim 1 wherein the reaction zone is substantially free of chloride ions and chloride compounds.

6. The process of claim 1 wherein the metal of the catalyst comprises rhodium.

7. The process of claim 1 wherein the heterocyclic nitrogen stabilizing agent comprises at least one imidazole, pyrazole, indazole, 1,2-diazine, 1,3,5-triazole, or benzimidazole.

8. The process of claim 1 wherein the heterocyclic nitrogen stabilizing agent is a benzimidazole.

9. The process of claim 1 wherein the heterocyclic nitrogen stabilizing agent comprises benzimidazole or benzotriazole.

10. The process of claim 6 wherein the heterocyclic nitrogen stabilizing agent is benzimidazole.

11. The process of claim 1 wherein the heterocyclic nitrogen stabilizing agent comprises at least one unfunctionalized nitrogen having a lone pair of electrons capable of forming a complex with the metal.

12. The process of claim 1 wherein the heterocyclic nitrogen stabilizing agent is an aromatic heterocyclic nitrogen stabilizing agent.

* * * * *